United States Patent [19]

Perrine et al.

[11] Patent Number: 6,011,000
[45] Date of Patent: Jan. 4, 2000

[54] COMPOSITIONS FOR THE TREATMENT OF BLOOD DISORDERS

[76] Inventors: Susan P. Perrine; Douglas V. Faller, both of 27 Harding Ave., Braintree, Mass. 02184

[21] Appl. No.: 08/470,831

[22] Filed: Jun. 6, 1995

Related U.S. Application Data

[63] Continuation of application No. 08/398,588, Mar. 3, 1995.

[51] Int. Cl.$^7$ .......................... A61K 38/17; A61K 38/18; A61K 38/22
[52] U.S. Cl. .................. 514/2; 514/4; 514/513; 514/563; 514/570
[58] Field of Search ................ 514/2, 4, 513, 514/563, 570

[56] References Cited

U.S. PATENT DOCUMENTS

| | | | |
|---|---|---|---|
| 3,471,513 | 10/1969 | Chinn et al. | 260/326.3 |
| 3,904,612 | 9/1975 | Nagasawa et al. | 260/240 J |
| 4,008,323 | 2/1977 | Cousse et al. | 424/250 |
| 4,011,336 | 3/1977 | Amann et al. | 424/304 |
| 4,031,243 | 6/1977 | Aparicio et al. | 424/317 |
| 4,058,558 | 11/1977 | Cousse et al. | 260/515 A |
| 4,131,617 | 12/1978 | Esanu | 260/465 |
| 4,176,193 | 11/1979 | Esanu | 424/304 |
| 4,234,599 | 11/1980 | Van Scott et al. | 424/279 |
| 4,671,901 | 6/1987 | Green | 260/404.5 |
| 4,699,926 | 10/1987 | Abraham et al. | 514/563 |
| 4,704,402 | 11/1987 | Abraham et al. | 514/543 |
| 4,731,381 | 3/1988 | Abraham et al. | 514/571 |
| 4,732,914 | 3/1988 | Morton, Jr. | 514/530 |
| 4,735,967 | 4/1988 | Neesby | 514/557 |
| 4,751,244 | 6/1988 | Abraham et al. | 514/563 |
| 4,822,821 | 4/1989 | Perine | 514/557 |
| 4,880,624 | 11/1989 | Metcalf et al. | 424/84 |
| 4,925,873 | 5/1990 | Friedhoff et al. | 514/469 |
| 4,952,560 | 8/1990 | Kigasawa et al. | 514/2 |
| 4,965,251 | 10/1990 | Stamatoyannopoulos | 514/8 |
| 4,997,815 | 3/1991 | Perrine et al. | 514/8 |
| 5,023,251 | 6/1991 | Sattler et al. | 514/179 |
| 5,025,029 | 6/1991 | Perrine | 514/381 |
| 5,032,507 | 7/1991 | Yu et al. | 435/29 |
| 5,039,703 | 8/1991 | Breuer | 514/557 |
| 5,081,124 | 1/1992 | Hughes | 514/259 |
| 5,137,734 | 8/1992 | Spiegeman et al. | 424/574 |
| 5,185,436 | 2/1993 | Villa et al. | 536/4.1 |
| 5,199,942 | 4/1993 | Gillis | 604/4 |
| 5,208,333 | 5/1993 | Paul et al. | 544/134 |
| 5,258,367 | 11/1993 | Bazer et al. | 514/6 |
| 5,270,458 | 12/1993 | Lemischka | 536/23.5 |
| 5,378,716 | 1/1995 | Hamanaka et al. | 514/333 |

FOREIGN PATENT DOCUMENTS

| | | |
|---|---|---|
| 1209037 | of 1986 | Canada . |
| 0224599 | 11/1985 | European Pat. Off. . |
| 0371789 | 11/1989 | European Pat. Off. . |
| 0617966 | 11/1989 | European Pat. Off. . |
| WO 93/07866 | 4/1993 | European Pat. Off. . |
| 50089335 | 7/1975 | Japan . |
| 61-180740 | 8/1986 | Japan . |
| 2126082 | 8/1983 | United Kingdom . |
| WO 92/04913 | 4/1992 | WIPO . |
| WO 93/18761 | 9/1993 | WIPO . |

*Primary Examiner*—Samuel Barts
*Assistant Examiner*—Rosalynd Keys
*Attorney, Agent, or Firm*—Ronald I. Eisenstein; David S. Resnick

[57] ABSTRACT

The invention relates to compositions containing chemical compounds and compositions containing steel factor which stimulate the expression of hemoglobin or globin protein such as embryonic or fetal globin, or the proliferation of hemoglobin expressing and other cells. These compositions can be used to treat or prevent the symptoms associated with anemia, sickle cell diseases, thalassemia and other blood disorders. The invention also relates to methods for administering these compositions to patients and to medical aids for the treatment and prevention of blood and other disorders.

10 Claims, 12 Drawing Sheets

COMPOSITIONS FOR THE TREATMENT OF BLOOD DISORDERS

This application is a continuation application of prior application Ser. No. 08/398,588, filed Mar. 3, 1995.

RIGHT IN THE INVENTION

This invention was made with support from the United States government under grant numbers HL-37118, HL-45940, HL-20895 and HL-15157, awarded by the National Institutes of Health, and grant number 000831, awarded by the United States Food & Drug Administration, and the United States government has certain rights in the invention.

BACKGROUND

1. Field of the Invention

The invention relates to compositions useful in the treatment and prevention of blood disorders such as anemia, thalassemia and sickle cell disease. Compositions comprise proteins or chemicals that stimulate the specific expression of a globin protein or the proliferation or development of hemoglobin expressing or other myeloid cells. The invention also relates to methods and medical aids which utilize these compositions to ameliorate symptoms associated with blood disorders.

2. Description of the Background

Hematopoiesis, or the formation of blood cells, begins in the developing human embryo as clusters of stem cells called blood islands. These cells appear in the yolk sac at about the third week of development and, at about the third month, migrate to the developing liver which becomes the principal site of blood cell formation. Although the spleen, lymph nodes and bone marrow all make small contributions to blood cell development, not until the fourth month does the bone marrow become the principal site of hematopoiesis. At birth, virtually all blood cells originate from the bone marrow. Although small foci of blood-forming cells sometimes persist in the liver for longer periods of time, hepatic blood cell formation has decreased to a trickle. At this time, all of the marrow is actively forming blood cells and continues to do so until after puberty when, at about 18 years of age, the principal sites of blood cell formation become the marrow of the vertebrae, ribs, sternum, skull, pelvis and the proximal epiphyseal regions of the femur and humerus. These areas represent only about half of the available marrow. The cavities which remain are filled with yellow-fatty tissues.

In the adult, hematopoiesis involves the bone marrow, the lymph nodes and the spleen. These organs and associated tissues are traditionally divided into myeloid and lymphoid tissue-types. Myeloid tissues and the cells derived from the myeloid tissue include the erythrocytes, platelets, granulocytes and monocytes. Lymphoid and lymphoid-derived tissues include the thymus, lymph nodes and spleen. The myeloid/lymphoid division is somewhat artificial as these two types of tissues are believed to originate from a single pluripotent stem cell.

Lymphoid and myeloid stem cells, formed from division of the pluripotent cell, are precursors for all subsequent cell types (FIG. 1). The committed cell-types for the lymphoid stem cell include the pro-T cells which form mature T cells and the pro-B cells which differentiate into plasma cells. Intermediate cell types can be distinguished based on cell-surface phenomenon such as the expression of immunoglobulin heavy and light chain, Ia protein and other cell surface markers. The three committed cell-types for the myeloid stem cell include E/mega cells which differentiate into the erythrocyte-burst forming unit (BFU-E) followed by the erythrocyte-colony forming unit cells (CFU-E) and megakaryocyte-CFU cells (CFU-mega), granulocyte/macrophage-CFU cells (CFU-G/M) which differentiate into CFU-G and CFU-M cells, and the eosinophil-CFU cells (CFU-Eo) which ultimately form mature eosinophils. Although these committed cell types reside mainly in the marrow, some circulate throughout the body in the blood stream.

The bone marrow provides a unique environment for pluripotent and committed cells. It contains both structural and humoral components that have yet to be successfully duplicated in culture. The marrow cavity itself is a network of thin-walled sinusoids lined with endothelial cells. Between the walls of bone are clusters of hematopoietic cells and fat cells constantly fed by mature blood cells entering through the endothelium. Differentiated cells ready to function within the circulatory system depart the cavity in a similar fashion.

The relative proportions of cell types in the bone marrow have a myeloid/erythroid ratio of about three to one comprising about 60% granulocytes and their precursors, about 10% lymphocytes and their precursors, about 20% erythrocytes and their precursors, and about 10% unidentified cells. The predominant myeloid cell types in the marrow cavity are the myelocytes, metamyelocytes and granulocytes. The predominant cell types in the erythroid compartment are the polychromatophilic and orhtochromic normoblasts. Under conditions of normal iron metabolism, about 30% to 40% of the normoblasts contain scattered ferritin granules. These cells are referred to as sideroblasts and the iron granules they contain are reservoirs drawn from as the cells insert iron into protoporphyrin to form heme. The production of heme and the production of globin are precisely balanced within the cell. If either is hindered or depressed, for whatever reason, excess ferritin accumulates in the sideroblasts. This increased iron accumulation can be visualized in the mitochondria, the loci of heme synthesis.

The major function of red blood cells is to transport oxygen to tissues of the body. Minor functions include the transportation of nutrients, intercellular messages and cytokines, and the absorption of cellular metabolites. Anemia, or a loss of red blood cells or red blood cell capacity, can be grossly defined as a reduction in the ability of blood to transport oxygen and may be acute or chronic. Chronic blood loss may be caused by extrinsic red blood cell abnormalities, intrinsic abnormalities or impaired production of red blood cells. Extrinsic or extra-corpuscular abnormalities include antibody-mediated disorders such as transfusion reactions and erythroblastosis, mechanical trauma to red cells such as micro-angiopathic hemolytic anemias, thrombotic thrombocytopenic purpura and disseminated intravascular coagulation. In addition, infections by parasites such as Plasmodium, chemical injuries from, for example, lead poisoning, and sequestration in the mononuclear system such as by hypersplenism can provoke red blood cell disorders.

Impaired red blood cell production can occur by disturbing the proliferation and differentiation of the stem cells or committed cells. Some of the more common diseases of red cell production include aplastic anemia, hypoplastic anemia, pure red cell aplasia and anemia associated with renal failure or endocrine disorders. Disturbances of the proliferation and differentiation of erythroblasts include defects in DNA synthesis such as impaired utilization of vitamin $B_{12}$ or folic acid and the megaloblastic anemias, defects in heme or globin synthesis, and anemias of unknown origins such as sideroblastic anemia, anemia associated with chronic infections such as malaria, trypanosomiasis, HIV, hepatitis virus or other viruses, and myelophthisic anemias caused by marrow deficiencies.

Intrinsic abnormalities include both hereditary and acquired disorders. Acquired disorders are those which have been induced through, for example, a membrane defect such as paroxysmal nocturnal hemoglobinuria. Hereditary disorders include disorders of membrane cytoskeleton such as spherocytosis and elliptocytosis, disorders of lipid synthesis such as an abnormally increased lecithin content of the cellular membrane, red cell enzyme deficiencies such as deficiencies of pyruvate kinase, hexokinase, glutathione synthetase and glucose-6-phosphate dehydrogenase. Although red blood cell disorders may be caused by certain drugs and immune system disorders, the majority are caused by genetic defects in the expression of hemoglobin. Disorders of hemoglobin synthesis include deficiencies of globin synthesis such as thalassemia syndromes and structural abnormalities of globin such as sickle cell syndromes and syndromes associated with unstable hemoglobins.

Hemoglobin comprises four protein chains, two alpha chains and two beta chains ($\alpha_2$ $\beta_2$), interwoven together, each with its own molecule of iron and with a combined molecular weight of about 68 kD. The hemoglobin macromolecule is normally glycosylated and upon absorbing oxygen from the lungs transforms into oxyhemoglobin ($HbO_2$). There are at least six distinct forms of hemoglobin, each expressed at various times during development. Hemoglobin in the embryo is found in at least three forms, Hb-Gower 1 ($\xi_2\epsilon_2$), Hb-Gower 2 ($\alpha_2\epsilon_2$), and Hb-Portand ($\xi_2\gamma_2$). Hemoglobin in the fetus comprises nearly totally HbF ($\alpha_2\gamma_2$), whereas hemoglobin in the adult contains about 96% HbA ($\alpha_2\beta_2$), about 3% $HbA_2$ ($\alpha_2\delta_2$) and about 1% fetal HbF ($\alpha_2\gamma_2$). The embryonic switch of globin expression from $\xi$ to $\alpha$ and from $\epsilon$ to $\gamma$ begins in the yolk sac. However, chains of embryonic $\xi$ and $\epsilon$ have been found in the fetal liver and complete transition to the fetal form does not occur until late in fetal development. The fetal switch from $\gamma$ to $\beta$ begins later in erythropoiesis with the amount of $\gamma$ globin produced increasing throughout gestation. At birth, $\beta$ globin accounts for about 40% of non-a globin chain synthesis and thereafter continues to rapidly increase. Neither the switch from embryonic to fetal or fetal to adult appears to be controlled through cell surface or known cytokine interactions. Control seems to reside in a developmental clock with the switch occurring at times determined only by the stage of fetal development.

Defects or mutations in globin chain expression are common. Some of these genetic mutations pose no adverse or only minor consequences to the person, however, most mutations prevent the formation of an intact or normal hemoglobin molecule through a functional or structural inability to effectively bind iron, an inability of the chains or chain pairs to effectively or properly interact, an inability of the molecule to absorb or release oxygen, a failure to express sufficient quantities of one or more globin chains or a combination of these malfunctions. For example, substitutions of valine for glutamic acid at the sixth position of the $\beta$ chain produces HbS and was found to occur in about 30% of black Americans. In the HbS heterozygote, only about 40% of total hemoglobin is HbS with the remainder being the more normal HbA.

Upon deoxygenation, HbS molecules undergo aggregation and polymerization ultimately leading to a morphological distortion of the red cells which acquire a sickle or holly-leaf shape. Sickling has two major consequences, a chronic hemolytic anemia and an occlusion of small blood vessels that results in ischemic damage to tissues. Further, when exposed to low oxygen tensions, polymerization converts HbS hemoglobin from a free-flowing liquid to a viscous gel. Consequently, the degree of pathology associated with sickle cell anemia can be correlated with the relative amount of HbS in the patient's system.

Individuals with severe sickle cell anemia develop no symptoms until about five to six months after birth. In these infants it was determined that fetal hemoglobin did not interact with HbS and, as long as sufficient quantities were present, could modulate the effects of HbS disease. This modulating effect of $\beta$ globin is also observed with other $\beta$ globin disorders, such as HbC and HbD, and other mutations of the $\beta$ chain. HbS polymerization is also significantly affected by the hemoglobin concentration of the cell. The higher the HbS concentration, the greater the chances for contact between two or more HbS molecules. Dehydration increases hemoglobin concentration and greatly facilitates sickling.

To some extent, sickling is a reversible phenomenon. With increased oxygen tensions, sickled cells depolymerize. This process of polymerization-depolymerization is very damaging to red cell membranes and eventually leads to irreversibly sickled cells (ISC) which retain their abnormal shape even when fully oxygenated. The average ISC survives for about 20 days in the body, as compared to the normal 120 day life span. Individuals with HbS syndromes have frequent infections, chronic hemolysis with a striking reticulocytosis and hyperbilirubinemia. The course of the disease is typically punctuated with a variety of painful crises called vaso-occlusive crises. These crises represent episodes of hypoxic injury and infarction in the organs, abdomen, chest, extremities or joints. Leg ulcers are an additional manifestation of the vaso-occlusive tendency of this disease. Central nervous system involvement is common producing seizures and even strokes. Aplastic crises, also common, represent a temporary cessation of bone marrow activity and may be triggered by infections, folic acid deficiency or both. Crises are episodic and reversible, but may be fatal. Damage from crisis episodes tends to be cumulative and even in those individuals with milder forms of sickle cell disorders, life-spans can be greatly reduced. Absent alternative intervention, patients typically die before the age of 30.

Anti-gelling compounds including clofibric acid ($ClC_6H_5OC(CH_3)_2COOH$), p-chloro phenoxy acetic acid ($ClC_6H_5OCH_2COOH$), and phenoxy acetic acid ($C_6H_5OCH_2COOH$) have been shown to prophylactically inhibit polymerization in artificially deoxygenated blood (D. J. Abraham et al., J. Med. Chem. 25:1015–17, 1982). It was speculated that these compounds may be useful in a narrow respect to prevent blood cell sickling in sickle cell disease. Such treatments may potentially decrease the frequency of symptomatic episodes caused by vaso-occlusive crises if enough of the chemical can be administered to bind all hemoglobin in the body.

The thalassemia syndromes are a heterogenous group of disorders all characterized by a lack of or a decreased synthesis of the globin chains of HbA. Deficiencies of $\beta$-globin expression are referred to as $\beta$-thalassemias and deficiencies of $\alpha$-globin, $\alpha$-thalassemias. The hemolytic consequences of deficient globin chain synthesis result from decreased synthesis of one chain and also an excess of the complementary chain. Free chains tend to aggregate into insoluble inclusions within erythrocytes causing premature destruction of maturing erythrocytes and their precursors, ineffective erythropoiesis, and the hemolysis of mature red blood cells. The underlying defects of hemoglobin synthesis have been elucidated over the years and largely reside in the nucleic acid sequences which express or control the expression of α or β globin protein.

Mammalian globin gene expression is highly regulated during development. The basic structure of the α and β globin genes are similar as are the basic steps in synthesis of α and β globin. There are at least five human a globin genes located on chromosome 16 including two adult a globin genes of 141 amino acids that encode identical polypeptides which differ only in their 3'-untranslated regions, one embryonic α gene, zeta (ξ), and at least two pseudo-alpha genes, psi zeta (ψξ) and omega alpha (ωα). Surprisingly, α-thalassemias tend to be less severe than β thalassemias. Homozygous pairs of β chains are believed to be more soluble than those derived from unpaired α chains. Consequently, the effects associated with free or improperly paired globin chains, which correlate with at least half of the clinical pathology associated with thalassemia, are minimized.

Hemoglobin H disease, a more severe form of α thalassemia, is a deletion of three of the four α globin genes. It is rarely found in those of African origin, but mostly in Asians. With only a single α gene, α chain expression is markedly depressed and there is an excess of β chains forming tetramers called HbH hemoglobin. HbH is unable to withstand oxidative stress and precipitates with vessels or is removed by the spleen. The most severe form of α thalassemia is hydrops fetalis and results from a deletion of all α globin genes. In the fetus, tetramers of γ globin develop (Hb Barts) that have an extremely high oxygen affinity and are unable to release oxygen to the tissues. Severe tissue anoxia results and leads to intrauterine fetal death.

The human β globin gene cluster includes one embryonic gene, epsilon (ε), two adult beta globin genes, beta (β) and delta (δ), two fetal beta globin genes G-gamma (G-γ) and A-gamma (A-γ), which differ by only one amino acid, and at least one pseudo-beta gene, psi beta (ψβ). All are expressed from a single 43 kilobase segment of human chromosome 11 (E. F. Fritsch et al., Nature 279:598–603, 1979). Fetal β-type globin, or γ globin, is expressed in the earliest stages of mammalian development and persists until about 32 to 34 weeks of gestation. At this stage, the adult forms of β globin begin to be expressed and substitute for the fetal proteins. Studies correlating clinical hematological results with the locations of various mutations that correspond to switching indicate that a region located upstream of the 5'-end of the δ-gene may be involved in the cis suppression of γ-gene expression in adults (E. F. Fritsch et al., Nature 279:598–603, 1979). The reason for this switch from fetal to adult protein is unknown and does not appear to provide any significant benefit to the adult.

Each β globin gene comprises three exons which encode about 146 amino acids, two introns and a 5'-untranslated region containing the promoter sequences. Biosynthesis of β globin begins with transcription of the entire gene followed with RNA processing of the message, removal of the introns by splicing, poly A addition, capping and post-transcriptional modifications. The mature mRNA molecule is exported from the nucleus and translated into β globin. Defects in each of these functions have been found associated with specific thalassemias. Identified mutations include single-nucleotide deletions, insertions and substitutions, frame shift mutations, deletions of entire segments of coding or controlling regions, improper termination signals, aberrant splicing signals, and multiple mutations. $β°$-thalassemias are characterized by a complete absence of any β globin chains. $β^+$-thalassemias are characterized by a detectable presence of a reduced amount of β chains.

There are three principal categories of β-thalassemia, thalassemia major, thalassemia intermedia and thalassemia minor. Patients with thalassemia minor may be totally asymptomatic and are genotypically $β^+/β$ or $β°/β$. Although red cell abnormalities can be detected, symptoms are mild. Thalassemia intermedia patients are most often genotypically $β^+/β^+$ or $β°/β^+$ and present severe symptoms which can be alleviated with infrequent blood transfusions. In contrast, thalassemia major patients are genotypically $β°/β°$, $β°/β^+$ or $β^+/β^+$, and require regular and frequent transfusions. Children suffer from severe growth retardation and die at an early age from the profound effects of anemia. Those that survive longer suffer from morphological changes. The face becomes distorted due to expansion of marrow within the bones of the skull, hepatosplenomegaly ensues, there is a delayed development of the endocrine organs including the sexual organs, and a progressive iron overload with secondary hemochromatosis.

There are two direct consequences of β-thalassemia. First, there is an inadequate formation of HbA and, therefore, an impaired ability to transport oxygen. There are also multiple effects attributable to an imbalance between α and β chain synthesis. Surprisingly, the pathological consequences of globin chain imbalance appears to be the mote severe. Free α chains form unstable aggregates that precipitate within red cell precursors in the form of insoluble inclusions. These inclusions damage cellular membranes resulting in a loss of potassium. The cumulative effect of these inclusions on the red blood cells is an ineffective erythropoiesis. An estimated 70% to 85% of normoblasts in the marrow are eventually destroyed. Those that do escape immediate destruction are at increased risk of elimination by the spleen where macrophages remove abnormal cells. Further, hemolysis triggers an increased expression of erythropoietin which expands populations of erythroid precursors within bone marrow and leads to skeletal abnormalities. Another severe complication of β thalassemia is that patients tend to have an increased ability to absorb dietary iron. As most treatments for thalassemia involve multiple transfusions of red blood cells, patients often have a severe state of iron overload damaging all of the organs and particularly the liver. To reduce the amount of iron in their systems, iron chelators are typically administered. Although helpful, patients succumb at an average of between about 17 to 35 years of age to the cumulative effects of the disease and iron overload.

Genotypic variation in healthy individuals have been identified- wherein adult β globin is not formed, but severe complications are avoided. These patients constituitively express fetal or γ globin protein in amounts sufficient to substitute for the missing β globin protein. This hereditary persistence of fetal hemoglobin (HPFH) may involve one or both of the fetal β-globin genes, A-γ and G-γ. Apparently, consistent production of either γ-globin protein accomplishes the necessary functions, at least in the short term, of the abnormal or missing β-globin protein (R. Bernards et al., Nuc. Acids Res. 8:1521–34, 1980).

A variety of small molecules have been shown to effect hemoglobin or fetal globin expression. Early experiments demonstrated that acetate ($CH_3COOH$), propionate ($CH_3CH_2COOH$), butyrate ($CH_3CH_2CH_2COOH$) and isobutyrate ($CH_3CH(CH_3)COOH$) all induced hemoglobin synthesis in cultured Friend leukemia cells (E. Takahashi et al., Gann 66:577–80, 1977). Additional studies showed that polar compounds, such as acid amides, and fatty acids could stimulate the expression of both fetal and adult globin genes in murine erythroleukemia cells (U. Nudel et al., Proc. Natl. Acad. Sci. USA 74:1100–4, 1977). Hydroxyurea ($H_2NCONHOH$), another relatively small molecule, was found to stimulate globin expression (N. L. Ietvin et al., N. Engl. J. Med. 310:869–73, 1984). Stimulation, however, did not appear to be very specific to fetal globin (S. Charache et al., Blood 69:109–16, 1987). Hydroxyurea is also a well-known carcinogen making its widespread and long term use as a pharmaceutical impractical.

Expression from the γ-globin genes has been successfully manipulated in vivo and in vitro using agents such as cytosine arabinoside (AraC), a cytotoxic agent that induces fetal reticulocyte production (P. Constantoulakis et al., Blood 74:1963–71, 1989), and 5-azacytidine (AZA), a well-known DNA methylase inhibitor (T. J. Ley et al., N. Engl. J. Med. 307:1469–75, 1982). Continuous intravenous administration of AZA produced a five- to seven-fold increase in γ globin mRNA of bone marrow cells (T. J. Ley et al., Blood 62:370–380, 1983). Additional studies have shown that there are significant alterations in the population of stem cells in the bone marrow after AZA treatment (A. T. Torrealba-De Ron et al., Blood 63:201–10, 1984). These experiments indicate that AZA's effects may be more attributable to reprogramming and recruitment of erythroid progenitor cells than to any direct effects on specific gene expression. Many of these agents including AZA, AraC and hydroxyurea are myelotoxic, carcinogenic or teratogenic making long-term use impractical.

One of the major breakthroughs in the treatment of hemoglobinopathies was made when it was discovered that butyric acid (butanoic acid; $CH_3CH_2CH_2COOH$) accurately and specifically stimulated transcription of the human fetal (γ) globin gene (G. A. Partington et al., EMBO J. 3:2787–92, 1984). These findings were quickly confirmed in vivo wherein it was shown that pharmacological doses of butyric acid greatly increased expression of fetal globin in adult chickens rendered anemic by injections with phenylhydrazine (G. D. Ginder et al., Proc. Natl. Acad. Sci. USA 81:3954– 58, 1984). Selective transcriptional activation was again thought to be due to hypo-methylation of the embryonic gene (L. J. Burns et al., Blood 72:1536–42, 1988). Others speculated that histone acetylation, a known effect of butyric acid, may be at least partly responsible for increased fetal gene expression (L. J. Burns et al., EMBO J. 3:2787, 1984).

Over 50 derivatives of butyric acid have since been found to be effective in stimulating fetal globin production (S. P. Perrine et al., Biochem. Biophys. Res. Commun. 148:694–700, 1987). Some of these include butyric acid salts such as sodium and arginine butyrate, α-amino-n-butyric acid (butyramide; $CH_3CH_2CH_2CONH_2$), and isobutyramide ($CH_3CH(CH_3)CONH_2$). Although promising in pilot clinical studies, treated patients were unable to maintain adequate levels of fetal globin in their system. It was later determined that many of these forms of butyric acid had extremely short-half lives. Oxidation in the serum, clearance by hepatocytes and filtration through the kidneys rapidly eliminated these agents from the patient's system. With others, patients rapidly developed tolerance or metabolites of compounds had the opposite desired effect.

Recently, a number of aliphatic carboxylic acids were tested for their ability to specifically increase fetal globin expression in K562 human erythroleukemia cells (S. Safaya et al., Blood 84:3929–35, 1994). Although longer chains were considered toxic to cells, propionate ($CH_3CH_2COOH$) and valerate (pentanoic acid; $CH_3CH_2CH_2CH_2COOH$) were found to be most effective. Butyrate ($CH_3(CH_2)_2COOH$), caproate ($CH_3(CH_2)_4COOH$), caprylate ($CH_3(CH_2)_6COOH$), nonanoate ($CH_3(CH_2)_7COOH$), and caprate ($CH_3(CH_2)_8COOH$) produced much less of an effect. Phenyl acetate ($C_6H_5CH_2COOH$) and its precursor, 4-phenyl butyrate ($C_6H_5CH_2CH_2CH_2COOH$), were found to decrease fetal globin expressing reticulocyte proliferation, but increase relative proportions of fetal globin per cell in cultured erythroid progenitor cells (E. Fibach et al., Blood 82:2203–9, 1993). Acetate ($CH_3COOH$), a metabolic product of butyrate catabolism, increased both erythrocyte precursor populations and also fetal globin synthesis. However, these studies also demonstrated that positive effects could only be maintained for very short periods of time (B. Pace et al., Blood 84:3198–204, 1994).

Other methodologies to increase fetal globin expression have focused on recruitment and reprogramming of erythroid progenitor cells to express fetal globin Agents tested in vivo or in vitro using this approach include hematopoietic growth factors such as erythropoietin (EPO) (Al-Khatti et al., Trans. Assoc. Am. Physicians 101:54, 1988; G. P. Rodgers et al., N. Engl. J. Med. 328:73–80, 1993), granulocyte/macrophage-colony stimulating factor (GM-CSF) (M. Giabbianeri et al., Blood 74:2657, 1989), and interleukin-3 (IL3) (A. R. Migliaccio et al., Blood 76:1150, 1990). Each of these factors were found to increase fetal globin synthesis in tissue culture cells.

Other agents shown to affect fetal globin expression include activin and inhibin. Inhibin, a disulfide linked hormone of two subunits, suppresses secretion of follicle-stimulating hormone from the pituitary gland. Activin, sometimes referred to as erythroid differentiating factor (EDF) or follicle-stimulating hormone releasing protein (FRP), is also a hormone and both of these macromolecules induced hemoglobin accumulation in cultured human erythrocytes (S. P. Perrine et al., Blood 74:114a, 1989). Recently, studies have shown that steel factor, a product of the mouse steel locus (D. M. Anderson et al., Cell 63:235–43, 1990), is also capable of influencing fetal globin synthesis in erythroid progenitors (B. A. Miller et al., Blood 79:1861–68, 1992).

Several studies have focused on the mechanism whereby butyric acid and other small organic molecules have been able to stimulate fetal globin expression (R. Oliva et al., Nuc. Acids Res. 18:2739, 1990). Experiments with cells in culture have indicated that butyric acid may act by increasing the level of histone acetylation by, possibly, decreasing the activity of one or more histone deacetylase. Resulting histone hyperacetylation may produce nucleosome unfolding and thereby increased gene expression. Other studies have indicated that hypo-methylation of the area of DNA around the β gene complex correlates with increased γ globin gene expression in thalassemic patients (S. Charache et al., Proc. Natl. Acad. Sci. USA 80:4842–46, 1983). Alternatively, butyric acid and other small molecules may function to increase specific gene expression by acting directly on agents which regulate transcription, the so-called transcription factors. These factors bind to sequence-specific sites along the genome at areas which control the expression of proximally located genes.

In contrast to the human alpha globin gene locus, the beta locus has been analyzed in great detail due, in part, to the identification of multiple mutations of beta globin genes in HPFH patients. The beta locus contains a large upstream sequence referred to as the locus control region (LCR), extending 8–16 kbp 5' of the epsilon gene. This sequence is divided into four DNase hypersensitive sites, HSS I–IV, that contain enhancer sequences, silencer sequences, transcription factor binding sites and other cis acting sequences (W. C. Forrester et al., Proc. Natl. Acad. Sci. USA 86:5439, 1989). Each of the genes of the beta globin cluster contains its own promoter which acts in concert with enhancer elements in the LCR. In fact, deletion of the LCR results in a thalassemic syndrome with little to no beta globin expression. These results indicate that the beta globin gene expressed may exert a competitive interaction over the LCR so that its enhancer effect is only available to a single gene at any given time of development (P. Fraser et al., Genes Dev. 7, 106–13, 1993).

A number of transcription factors have been identified in the beta locus which are thought to alter the level of beta globin gene expression. An enhancer element of the LCR has been shown to contain a pair of binding sites for nuclear factor E2 (NF-E2) which overlaps a tandem set of binding sites for transcription factor AP-1 (N. C. Andrews et al., Nature 362:722, 1993). NF-E2, a hematopoietic-specific basic leucine zipper protein, and AP-1 binding sites have been located on a variety of globin genetic elements (P. A. Ney et al., Genes Dev. 4:993, 1990). Recently, a conserved sequence (CS) located upstream of the AP-1/NF-E2 site has been proposed to augment enhancing activity (S. Safaya et al., Blood 84:3929–35, 1994).

Additional factors that bind to elements within the promoters of the beta globin cluster have been identified. The CAT box displacement protein (CDP) binds to the sequence CAAT, located about 50 bp upstream of many gene promoters. Another fairly ubiquitous transcription factor, SP1, binds to positions −140 and −202, and possible additional sites as well. TAFII110 has been shown to binds to the TATA box of many of the beta globin promoters (T. Hoey et al., Cell 72:247–60, 1993). Transcription factors GATA-1, binds to the transcription initiation site (GATA) and may be displaced by TFIID when forming an active initiation complex (M. C. Barton et al., Genes Dev. 7:1796–809, 1993). Another erythroid-specific factor, YY1, binds to at least 11 sites distributed throughout the globin regulatory region.

Recently, a factor has been identified that may be involved in the developmental regulation of hemoglobin expression. This factor, termed the stage selector protein (SSP), binds to a site located about 50–60 bps upstream of the gamma globin promoter referred to as the stage selector element (SSE) (S. M. Jane et al., EMBO J. 14:97–105, 1995). The SSE is also the site where a number of mutations have been found in HPFH syndrome patients. SSP has been purified from K562 cell nuclear extracts and its relatively fetal and erythroid specificity has been attributed to a heterodimeric partner protein of 40–45 kD termed CP2 which selectively allows assembly of the SSP complex on the SSE, and also on sites within the $\epsilon$ promoter, and subsequent interaction with RNA polymerase.

SUMMARY OF THE INVENTION

The invention overcomes the problems and disadvantages associated with current strategies and designs and provides new compositions, methods and aids for the treatment and prevention of blood disorders.

One embodiment of the invention is directed to compositions that contain chemical compounds which stimulate the proliferation of hemoglobin producing cells, the expression of hemoglobin or the expression of embryonic or fetal globin in mammalian cells. Chemical compounds have the structure $R_1$—C(O)—$R_2$—$R_3$, phenyl—$R_5$—$R_6$—$R_7$ or phenyl—$R_9$—$R_{10}$ wherein; $R_1$ is $SH_2$, $NH_2$ or OH; $R_2$ is a branched or linear alkyl; $R_3$ is $CONH_2$, $COSH_2$, COOH, $COOR_4$, $C(O)R_4$ or $OR_4$; $R_4$ is a branched or linear alkyl; $R_5$ is O, SH or NH; $R_6$ is a branched or linear alkyl; $R_7$ is COOH, $CONH_2$, $COSH_2$, $COOR_8$, $C(O)R_8$ or $OR_8$; $R_8$ is a branched or linear alkyl; $R_9$ is a branched alkyl of 2 to 4 carbon atoms or an unbranched alkyl of 2 or 4 carbon atoms; $R_{10}$ is COOH, $CONH_2$, $COSH_2$, $COOR_{11}$, $C(O)R_{11}$ or $OR_{11}$; and $R_{11}$ is a branched or linear alkyl. Useful chemical compounds include cinnamic acid, hydrocinnamic acid, α-methyl hydrocinnamic acid, phenoxy acetic acids and amides, thiophenoxy acetic acid and acid amide, thiophenoxy propionic acid, thiophenoxy butyric acid, methoxy acetic acid, phenyl butyric acid, fumaric acid, fumaric acid monoamide and diamide, fumaric acid monoethyl ester, succinic acid, succinic acid monoamide (succinamic acid), succinic acid diamide (succinamide), ethyl phenyl acetate and derivatives and combination of these chemicals. Additional chemical compounds which are useful in compositions of the invention include acids and amides of butyric acid ethyl ester, trifluorobutyric acid, tributyrin, ethylphenyl acetic acid, indol-3-butyric acid and indol-3-propionic acid.

Another embodiment of the invention is directed to compositions which contain chemical compounds that stimulate the proliferation of hemoglobin producing and other types of cells, the expression of hemoglobin or the expression of embryonic or fetal globin in mammalian cells, but do not decrease or otherwise adversely affect cell viability. Such chemical compounds include butyric acid ethyl ester, methoxy acetic acid, cinnamic acid, hydrocinnamic acid, methyldihydrocinnamic acid, phenoxy acetic acids and amide, thiophenoxyacetic acid, and amines and amides of these compounds. Cell viability may be assayed by DNA fragmentation assays or cell division assays, or by measuring the amount of nucleic acid or protein synthesis which occurred in treated cells as compared to untreated cells. Cells tested may be normal healthy cells, patient cells to be treated or cells in tissue culture.

Another embodiment of the invention is directed to methods for the treatment of blood disorders. Compositions containing an effective amount of one or more agents which stimulate the proliferation of hemoglobin producing cells or the expression of embryonic or fetal globin from cells are administered to patients. Patients may be any mammal such as a human. Administration may be by parenteral or non-parenteral means, but is preferably oral or intravenous. Treatment may be for short periods of time or continuous throughout the lifetime of the patient.

Another embodiment of the invention is directed to methods for the treatment of blood disorders comprising the administration of compositions containing therapeutically effective amounts of steel factor to a patient. Steel factor increases the proportion or number of reticulocytes that express embryonic or fetal globin and the amount of embryonic or fetal globin expressed per cell.

Another embodiment of the invention is directed to methods for regulating the expression of a globin gene such as an embryonic or fetal globin gene or an at least partially functional pseudo-globin gene in mammalian cells. Treated cells, or products expressed from these cells, can be harvested and introduced or reintroduced to a patient to treat or prevent a blood disorder.

Another embodiment of the invention is directed to methods for regulating the proliferation of hemoglobin expressing cells. Cells in culture or in patients are exposed to compositions of the invention and induced to proliferate. Proliferating cells may be stem cells, committed cells such as BFUs or CFUs, or mature reticulocytes. These cells can be used to treat blood disorders or to produce large quantities of products which are expressed from bacterial or mammalian cells.

Another embodiment of the invention is directed to methods for the prevention of blood disorders. Compositions containing an effective amount of agents which stimulate the proliferation of hemoglobin producing cells or the expression of embryonic or fetal globin are administered to patients suspected of having a blood disorder. The patient may be any mammal such as a human and is preferably an adolescent, child or infant. Administration may be by any route including parenteral and nonparenteral routes, but is preferably oral or intravenous. Treatment may be for short periods of time or continuous throughout the lifetime of the patient.

Another embodiment of the invention is directed to purified transcription factors, antibodies directed against these factors and the binding elements for these factors. Factors or the expression of these factors can be manipulated to stimulate expression of specific globin genes and some bind to sites in the proximal promoter region of globin genes. Hemoglobin and globin expression can be influenced by administration of compositions of the invention to mammalian cells to alter binding of the factor to the globin promoter. These factors can be cloned and recombinant protein or anti-sense RNA expressed from vectors in transformed cells. Additionally, binding site sequences can also be used to competitively inhibit factor binding.

Another embodiment of the invention is directed to a method for increasing a hemoglobin content of blood comprising administering a composition to a patient containing a chemical compound of the structure: $R_1$—C(O)—$R_2$—$R_3$, phenyl—$R_5$—$R_6$—$R_7$ or phenyl—$R_9$—$R_{10}$, as described above. Hemoglobin content of blood so treated is increased greater than about 1%, which is sufficient to treat or prevent blood and other disorders in the same or a different patient. Alternatively, the patient can be treated and the patient's blood collected at peak times of hemoglobin or globin production, collected and stored, and administered to another patient or re-administered to the same patient. Such treatments would be useful therapies for those being treated with radiation therapy, chemotherapy, bone marrow transplants, blood diseases, such as sickle cell disease and thalassemia, and other disorders which would be alleviated with an increased blood hemoglobin content.

Another embodiment of the invention is directed to methods for treating or preventing a neoplastic disorder in a patient. Treatment involves administration of compositions of the invention. Compositions contain one or more of the above-described chemical compounds. Administration may be by either parenteral or non-parenteral routes and for short periods of time or continuous for the lifetime of the patient.

Another embodiment of the invention is directed to aids for the treatment of human disorders. Aids contain compositions of the invention, which may be liquids or solids, in predetermined concentrations and amounts. An aid, such as an infuser, delivers compositions to the patient sporadically or continuously as desired. Aids may further comprise mechanical or electrical controlled devices to regulate dosage administration.

Other objects and advantages of the invention are set forth in part in the description which follows, and in part, will be obvious from this description, or may be learned from the practice of the invention.

DESCRIPTION OF THE INVENTION

Figure 1:
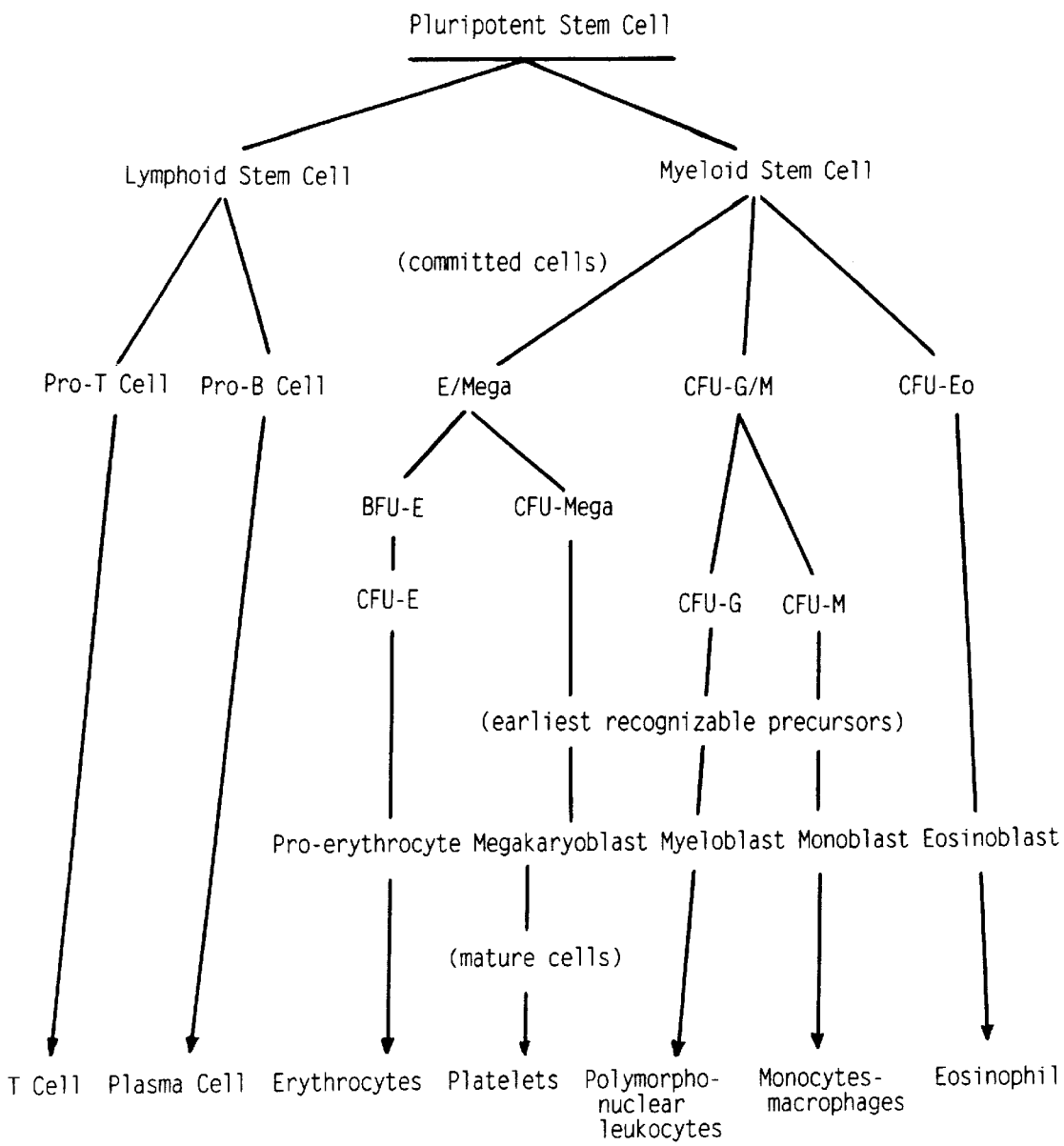
FIG. 1 Cell types and ontogenic relationships of the lymphoid and myeloid development systems.

As embodied and broadly described herein, the present invention is directed to pharmaceutical compositions useful for the treatment and prevention of disorders including blood disorders such as anemias, sickle cell syndromes and thalassemia, to methods for using these compositions, and to aids which contain these compositions. The invention also relates to macromolecules including protein factors and genetic elements, and molecular methods whereby globin gene expression can be regulated.

Disorders of globin gene expression are extremely varied and produce a wide range of clinical manifestations. Consequences to the individual range from a mild weakness after exertion to a prolonged and protracted series of crises leading to an early death. Increased expression of the hemoglobin macromolecule or specific globin peptide chains has been shown to alleviate many of these manifestations, improving and prolonging the life of the afflicted individual. Some of the more successful treatments involve the administration of biologically active proteins or chemical compounds to promote hematopoiesis, to promote the proliferation of hemoglobin expressing cells or to increase or stimulate the expression of fetal globin protein. Although promising, these compositions have a number of drawbacks. Many substances are carcinogenic or mutagenic and prolonged use would pose serious risks to the patient. Some require continuous use at fairly high doses while others have short effective half-lives. Tolerance to the active ingredient often develops rendering the composition functionally useless. In addition to problems associated with tolerance, the substances themselves or their metabolic by-products or carriers quickly reach toxic levels in the patient's system which slow or inhibit blood cell proliferation or, these metabolites are themselves functionally detrimental. The chemical compounds are rapidly destroyed by catabolic enzymes, commonly found in the cells and serum such as aminases, oxidases and hydrolases. Many of these enzymes are also found in hepatic cells, the principal sites for cleansing of the blood. Those able to survive cellular and hepatic catabolic processes are quickly eliminated from the patient's system by nephrotic cells of the kidneys. Consequently, in vivo retention times for active compounds are extremely short and the ability to achieve any sort of sustained biological effect becomes nearly impossible or, at least, impractical.

One embodiment of the invention is directed to physiologically stable and safe pharmaceutical compositions useful in the treatment or prevention of blood disorders. Compositions contain one or more chemical compounds that increase the extent or magnitude of hematopoiesis, increase the proliferation of hemoglobin expressing and other cells, increase or balance the expression of globin proteins or increase or stimulate the specific expression of functional globin protein such as γ-globin. Stimulation of specific gene expression involves activation of transcription or translation promoters or enhancers, or alteration of the methylation pattern or histone distribution along the gene. Expression may also be stimulated by inhibition of specific transcription or translation repressors, activation of specific transcription or translation activation factors, or activation of receptors on the surface of particular populations of cells. Stimulation may recruit additional cells to marrow, reprogram differentiated cells to express hemoglobin or switch to the expression of an embryonic, fetal or other globin-like peptide. Stimulation may also activate a previously dormant or relatively inactive genes which substitutes for the defective or damaged gene products such as, for example, the post-natally suppressed genes which encode ε, δ or γ globin, which can substitute for adult β globin, or ξ globin which can substitute for a defective or deficient α globin.

Alternatively, certain compositions of the invention may be used to turn down the expression of those genes whose products are being over expressed and thereby disrupting the balanced production of normal globin proteins. Genes whose expression or whose balanced expression can be effected by compositions of the invention include the globin genes such as the various forms of the ξ-type genes, the ε-type genes, the α-type genes, the β-type genes, the δ-type genes, the γ-type genes and at least partially functional pseudo-globin genes.

The mechanism of action of chemical compounds of the invention involves effecting one or more of the processes of cell proliferation, cell recruitment, hemoglobin expression, heme synthesis or globin chain expression. Cell proliferation may be increased, for example, by stimulating stem cells, CFUs, BFUs, platelets, white blood cells or pro-erythrocyte colony growth, or decreased, for example, by effecting a cell's period in or ability to transverse a stage (S, $G_0$, $G_1$, M) of the cell cycle. Cell recruitment may be promoted through the expression of specific cytokines such as cell surface receptors or secreted factors. Hemoglobin expression can be increased or decreased by affecting heme expression, globin peptide expression, heme/globin peptide assembly, globin peptide glycosylation or globin transport through the golgi apparatus. Globin expression can be increased or decreased by altering chromatin and/or nucleosome structure to render a genetic element more or less susceptible to transcription, by altering DNA structure, for example, by methylation of G residues, by affecting the activity of cell-specific transcription or translation factors such as activators or repressors, or by increasing the rate of transcription or translation. For example, certain compositions of the invention including phenoxyacetic acid, methoxyacetic acid, butyric acid ethyl ester, cinnamic acid, hydrocinnamic acid and α-methyl cinnamic acid and hydrocinnamic acid stimulate binding or removal of transcription factors from the proximal promoter region of certain genes of the α- and β-globin gene clusters and thereby increase post-natally suppressed gene expression.

Compositions of the invention preferably increase the expression of hemoglobin, increase the expression of one or more embryonic or fetal globin genes or increase the number of hemoglobin expressing or fetal globin expressing reticulocytes. Preferably, compositions of the invention increase embryonic or fetal globin gene expression or embryonic or fetal reticulocyte counts greater than about 2%, more preferably greater than about 5%, and even more preferably greater than about 9%. For comparative purposes, a 4% increase in fetal globin gene expression equates to about 20% to 25% rise or increase in fetal globin in peripheral blood samples. Consequently, an increase of greater than about 1% fetal globin expression or about 1% fetal globin expressing cells can alleviate symptoms associated with beta globin disorders.

Hemoglobin expression, globin expression and cell proliferation can be assayed by measuring fold increases in expressed amounts of specific protein or numbers of specific cells in treated samples as compared to untreated controls. Utilizing this criteria, compositions of the invention preferably increase the amount of hemoglobin expression, the amount of globin expression, the number of hemoglobin expressing cells or the number of globin expressing cells by greater than or equal to about two-fold, preferably about four-fold and more preferably about eight-fold.

Chemical compounds which perform one or more of these biological functions have the structure $R_1$—C(O)—$R_2$—$R_3$, phenyl—$R_5$—$R_6$—$R_7$ or phenyl—$R_9$—$R_{10}$ wherein; phenyl is a six carbon benzyl ring or a hydroxylated six carbon ring; $R_1$ is $SH_2$, $NH_2$ or OH; $R_2$ is a branched or linear alkyl; $R_3$ is $CONH_2$, $COSH_2$, COOH, $COOR_4$, C(O)$R_4$ or $OR_4$; $R_4$ is a branched or linear alkyl; $R_5$ is O, SH or NH; $R_6$ is a branched or linear alkyl; $R_7$ is COOH, $CONH_2$, $COSH_2$, $COOR_8$, $C(O)R_8$ or $OR_8$; $R_8$ is a branched or linear alkyl; $R_9$ is a branched alkyl of 2 to 4 carbon atoms or an unbranched alkyl of 2 or 4 carbon atoms; $R_{10}$ is COOH, $CONH_2$, $COSH_2$, $COOR_{11}$, $C(O)R_{11}$ or $OR_{11}$; and $R_{11}$ is a branched or linear alkyl. Preferably, $R_2$ comprises between 1 to 8 carbon atoms and more preferably 1, 2, 3 or 4 carbon atoms. Preferably, $R_4$ comprises between 1 to 8 carbon atoms and more preferably 1, 2, 3 or 4 carbon atoms. Preferably, $R_6$ comprises between 1 to 8 carbon atoms and more preferably 1, 2, 3 or 4 carbon atoms. Preferably, $R_8$ comprises between 1 to 8 carbon atoms and more preferably 1, 2, 3 or 4 carbon atoms.

Examples of chemical compounds of the structure $R_1$—C(O)—$R_2$—$R_3$ include acids, monoamides and diamides of fumaric acid (HOOCCH=CHCOOH), fumaric add monoethyl ester, succinic acid ($HOOCCH_2CH_2COOH$) (succinamic acid and succinamide), 2,3-dimethyl succinic acid and methoxy acetic acid ($CH_3CH_2OCH_3$). Examples of chemical compounds of the structure phenyl—$R_5$—$R_6$—$R_7$ include acids and amides of phenoxyacetic acid ($C_6H_5OCH_2COOH$; $C_6H_5OCH_2COONH_3$), 2- and 3-thiophenoxy propionic acid ($C_6H_5SCH(CH_3)COOH$; $C_6H_5SCH_2CH_2COOH$), 2- and 3-phenoxy propionic acid ($C_6H_5OCH(CH_3)COOH$; $C_6H_5OCH_2CH_2COOH$), 2- and 3-phenyl propionic acid ($C_6H_5CH(CH_3)COOH$; $C_6H_5CH_2CH_2COOH$) and 2-thiophenoxy acetic acid ($C_6H_5SCH_2COOH$). Examples of chemical compounds of the structure phenyl—$R_9$—$R_{10}$ include acids and amides of cinnamic acid ($C_6H_5CH=CHCOOH$), dihydrocinnamic acid ($C_6H_5CH_2CH_2COOH$), methyl or 2,3-dimethyl dihydrocinnamic acid, phenyl acetate ethyl ester ($C_6H_5CH(CH_3)CH_2COCCH_2CH_3$) and 3-phenyl butyric acid ($C_6H_5CH(CH_3)CH_2COOH$). Additional chemical compounds of the invention which are not included in the above classification scheme include acids and amides of butyric acid ethyl ester ($CH_3CH_2CH_2COCH_2CH_3$), 4,4,4-trifluorobutyric acid ($CF_3CH_2CH_2COOH$), tributyrin ($CH_2(OCOCH_2CH_2CH_3)CH(OCOCH_2CH_2CH_3)$ $CH_2(OCOCH_2CH_2CH_3)$), ethylphenyl acetic acid ($CH_3CH_2C_6H_5CH_2COOH$), indol-3-propionic acid and indol-3-butyric acid.

Chemical compounds of the invention are preferably optically pure with a specific conformation (plus {+} or minus {−}), absolute configuration (R or S), or relative configuration (D or L). Particular salts such as sodium, potassium, magnesium, calcium, ammonium or lithium, or combinations of salts may also be preferred, however, certain salts may be more advantageous than others. For example, chemical compounds that require high doses may introduce too much of a single salt to the patient. Sodium is generally an undesirable salt because at high doses, sodium can increase fluid retention resulting in tissue destruction. In such circumstances, combinations of different salts or alternative salts can be used.

In addition to the above chemical compounds, compounds of the invention include derivatives of these chemicals. Derivatives are chemical or biological modifications of the parent compound and include analogs, homologs, next adjacent homologs and compounds based on any of the foregoing. Analogs include both structural and functional analogs. Functional analogs are those compounds which are functionally related to the activity of the parent compound. Structural analogs are those compounds related to the parent compound in the arrangement or number of carbon atoms. For example, such compounds may have double or triple covalent bonds wherein the parent has a single covalent bond. Homologs are those compounds which have the same number of carbon atoms as the parent compound, but further comprise additional moieties such as one or more phosphate groups ($PO_4$), sulfate groups ($SO_3$), amines and amides ($NH_3$), nitrate groups ($NO_2$), acidified or esterified carbon atoms or combinations thereof. Next adjacent homologs are those compounds with one more or less carbon atom. Related compounds include those compounds which have been modified such as by substitutions and/or additions. For example, compounds of the invention may be substituted with one or more halogens such as chlorine (Cl), fluorine (F), iodine (I), bromine (Br) or combinations of these halogens. As known to those of ordinary skill in the art, halogenation can increase the polarity, hydrophilicity or lipophilicity or a chemical compound which can be a desirable feature, for example, to transform a chemical compound into a composition which is more easily tolerated by the patient or more readily absorbed by the epithelial lining of the gastrointestinal tract. Such compositions could be orally administered to patients.

Therapeutically effective chemical compounds may be created by modifying any of the above chemical compounds so that after introduction into the patient, these compounds metabolize into active forms, such as the forms above, which have the desired effect on the patient. Compounds may also be created which metabolize in a timed-release fashion allowing for a minimal number of introductions which are efficacious for longer periods of time. Combinations of chemical compounds can also produce useful new compounds from the interaction of the combination. Such compounds may also produce a synergistic effect when used in combination with other known compounds or with other compounds of the invention.

Compositions of the invention may alternatively or in addition to the above compounds comprise a proteinaceous agent which will increase the extent or magnitude of hematopoiesis, increase the proliferation of hemoglobin expressing cells, increase or balance the expression of hemoglobin macromolecules or increase or stimulate the specific expression of alternate globin genes such as γ-globin. Such proteinaceous agents include steel factor, insulin, erythropoietin (EPO), interferon (IFN), insulin growth factor (IGF), stem cell factor (SCF), macrophage-colony stimulating factor (M-CSF), granulocyte-colony stimulating factor (G-CSF), GM-CSF, growth factors such as fibroblast-derived growth factor (FGF), epidermal growth factor (EGF) and platelet-derived growth factor (PDGF), bone morphogenic proteins (BMPs), the interleukins (IL) IL 1, IL-2, IL-3, IL-4, IL-5, IL-6, IL-7, IL-8, etc., activin also referred to as erythroid differentiation factor (EDF) or foricle-stimulating hormone releasing protein (FRP), inhibin, stem cell proliferation factor (SCPF) and active fragments, subunits, derivatives and combinations of these proteins. Erythropoietin, activin and SCF all stimulate the proliferation of stem cells, committed cells and erythroid progenitor cells, and can also stimulate the expression of embryonic globin, fetal globin or partly functional pseudo-globin expression. The hematopoietic factor, steel factor, also referred to as kit ligand, mast cell growth factor and stem cell factor, recruits and stimulates the proliferation of hemoglobin expressing cells and the specific expression of embryonic or fetal globin. Proteinaceous agents of the invention may also be aminated, glycosylated, acylated, neutralized, phosphorylated or otherwise derivatized to form compositions which are more suitable for the method of administration to the patient or for increased stability during shipping or storage.

Compositions of the invention are physiologically stable at therapeutically effective concentrations. Physiological stable compounds are compounds that do not break down or otherwise become ineffective upon introduction to a patient prior to having a desired effect. Compounds are structurally resistant to catabolism, and thus, physiologically stable, or coupled by electrostatic or covalent bonds to specific reagents to increase physiological stability. Such reagents include amino acids such as arginine, glycine, alanine, asparagine, glutamine, histidine or lysine, nucleic acids including nucleosides or nucleotides, or substituents such as carbohydrates, saccharides and polysaccharides, lipids, fatty acids, proteins, or protein fragments. Useful coupling partners include, for example, glycol such as polyethylene glycol, glucose, glycerol, glycerin and other related substances.

Physiological stability can be measured from a number of parameters such as the half-life of the compound or the half-life of active metabolic products derived from the compound. Compounds of the invention have in vivo half lives of greater than about fifteen minutes, preferably greater than about one hour, more preferably greater than about two hours, and even more preferably greater than about four hours, eight hours, twelve hours or longer. Although a compound is stable using this criteria, physiological stability can also be measured by observing the duration of biological effects on the patient. These effects include amelioration or elimination of patient symptoms, an increase in number or appearance of hemoglobin producing cells, or an alteration, activation or suppression of specific gene expression, such as, for example, the persistence of fetal globin chain expression in blood cells.

Symptoms may be clinically observed or biologically quantified. For example, observed symptoms are those which can be clinically perceived and include pathological alterations in cellular morphology such as red cell sickling, anemic crises, jaundice, splenomegaly, hepatomegaly, hemorrhaging, tissue damage due to hypoxia, organ dysfunction, pain such as angina pectoris, fatigue including shortness of breath, weakness and poor exercise ability, and pallor. Clinical symptoms which are important from the patient's perspective include a reduced frequency or duration, or elimination of the need for transfusions or chelation therapy. Quantifiable biological symptoms are those which can be more accurately measured such as anemia, enzyme activity, hematocrit and hemoglobin levels, decreased cell viability, ineffective erythropoiesis, abnormal reticulocyte count, abnormal iron loads, inadequate peripheral blood flow, anuria, dyspnea, hemolysis and specific gene expression. Other quantifiable biological activities include, for example, the ability to recruit and stimulate the proliferation of hemoglobin expressing cells, the ability to increase hemoglobin expression, the ability to balance α-type and β-type globin gene expression or the ability to increase expression of embryonic, fetal or at least partially functional pseudo-globin genes. Preferably, a stable compound of the invention has an in vivo half-life of greater than about 15 minutes, a serum half-life of greater than about 15 minutes, or a biological effect which continues for greater than 15 minutes after treatment has been terminated or the serum level of the compound has decreased by more than half.

Compositions of the invention are not significantly biotransformed, degraded or excreted by catabolic processes associated with metabolism prior to having their desired effect. Catabolic processes include deamination of aminases, hydrolysis of esters and amides, conjugation reactions with, for example, glycine or sulfate, oxidation by the cytochrome p450 oxidation/reduction enzyme system and degradation in the fatty acid pathway. Hydrolysis reactions occur mainly in the liver and plasma by a variety of non-specific hydrolases and esterases. Both deaminases and amidases, also localized in the liver and serum, carry out a large part of the catabolic process. Reduction reactions occur mainly intracellularly in the endoplasmic reticulum and transferases perform conjugation reactions mainly in the kidneys and liver.

The kidneys are the most important organs for elimination of chemical compounds and their metabolites from the body. Renal excretion requires one or more of the processes of glomerular filtration, active tubular secretion and passive tubular reabsorption. Many chemicals are transported independently through the membranes of the nephrons, while others require carriers and carrier specific systems. Many chemical compounds are excreted by the liver into bile and eventually the intestinal tract. Both processes are utilized by the body to promote clearance and rapidly eliminate unwanted chemical compounds from the patient.

Compositions of the invention should also be safe at effective dosages. Safe compositions are compositions that are not substantially toxic, myelotoxic, mutagenic or teratogenic at required dosages, do not cause adverse reactions or side effects, and are well tolerated. Although side effects may occur, safe compositions are those wherein the benefits achieved from their use outweigh disadvantages attributable to adverse side effects. Unwanted side effects include nausea, vomiting, hepatic or renal damage or failure, hypersensitivity, allergic reactions, cardiovascular problems, gastrointestinal disturbances, seizures and other central nervous system difficulties, fever, bleeding or hemorrhaging, serum abnormalities and respiratory difficulties.

Compositions of the invention useful for treating blood disorders preferably do not substantially affect the viability of a cell such as a normal mammalian cell, the cell being treated or effected by the chemical compound. Normal cell viability, the viability of an untransformed or uninfected cell, can be determined from analyzing the effects of the composition on one or more biological processes of the cell. Detrimental interference with one or more of these cellular processes becomes significant when the process becomes abnormal. Examples of quantitatable and qualifiable biological processes include the processes of cell division, protein synthesis, nucleic acid (DNA or RNA) synthesis, nucleic acid (principally DNA) fragmentation and apoptosis. Others processes include specific enzyme activities, the activities of the cellular transportation systems such as the transportation of amino acids by system A (neutral), system B (acidic) or system C (basic), and the expression of a cell surface protein. Each of these parameters is easily determined as significantly detrimental, for example, in tissue culture experiments, in animal experiments or in clinical studies using techniques known to those of ordinary skill in the art. Abnormal cell division, for example, can be mitosis which occurs too rapidly, as in a malignancy, or unstably, resulting in programmed cell death or apoptosis, detected by increased DNA degradation. The determination of abnormal cell viability can be made on comparison with untreated control cells. Compositions preferably increase normal cell viability. Increased cell viability can be determined by those of ordinary skill in the art using, for example, DNA fragmentation analysis. A decreased amount of fragmentation indicates that cellular viability is boosted. Determinations of increased or decreased viability can also be concluded from an analysis of the results of multiple different assays. Where multiple tests provide conflicting results, accurate conclusions can still be drawn by those of ordinary skill based upon the cell type, the correctness or correlation of the tests with actual conditions and the type of composition.

Compositions of the invention can be prepared in solution as a dispersion, mixture, liquid, spray, capsule or as a dry solid such as a powder or pill, as appropriate or desired. Solid forms may be processed into tablets or capsules or mixed or dissolved with a liquid such as water, alcohol, saline or other salt solutions, glycerol, saccharides or polysaccharide, oil or a relatively inert solid or liquid. Liquids administered orally may include flavoring agents such as mint, cherry, guava, citrus, cinnamon, orange, mango, or mixed fruit flavors to increase palatability. Pills, capsules or tablets administered orally may also include flavoring agents. Additionally, all compositions may further comprise agents to increase shelf-life, such as preservatives, anti-oxidants and other components necessary and suitable for manufacture and distribution of the composition. Compositions further comprise a pharmaceutically acceptable carrier. Carriers are chemical or multi-chemical compounds that do not significantly alter or effect the active ingredients of the compositions. Examples include water, alcohols such as glycerol and polyethylene glycol, glycerin, oils, salts such as sodium, potassium, magnesium and ammonium, fatty acids, saccharides or polysaccharides. Carriers may be single substances or chemical or physical combinations of these substances.

Another embodiment of the invention is directed to compositions comprising a chemical compound of the invention in combination with an agent known to positively affect hemoglobin expression or hemoglobin expressing cells. The agent may be a chemical compound such as acetic acid, butyric acid, D- or L-amino-n-butyric acid, α- or β-amino-n-butyric acid, arginine butyrate and isobutyramide, all disclosed in U.S. Pat. Nos. 4,822,821 and 5,025,029. Others include butyrin, 4-phenyl butyrate ($C_6H_5CH_2CH_2CH_2COOH$), phenylacetate ($C_6H_5CH_2COOH$), phenoxy acetic acid, disclosed in U.S. Pat. No. 4,704,402, and derivatives, salts and combination of these agents. Alternatively, the agent may be a hematopoietic protein such as erythropoietin, steel factor, insulin, an interleukin, a growth factor, hormones such as activin or inhibin, disclosed in U.S. Pat. Nos. 5,032,507 and 4,997,815, and active fragments and combinations of these proteins either with each other or with other chemical compounds. Such composition may have additive or synergistic effects. The above U.S. patents are hereby specifically incorporated by reference.

Another embodiment of the invention is directed to methods for the treatment of patients with blood disorder comprising the administration of one or more compositions of the invention. Compositions to be administered contain a therapeutically effective amount of a chemical compound or proteinaceous agent. A therapeutical effective amount is that amount which has a beneficial effect to the patient by alleviating one or more symptoms of the disorder or simply reduce premature mortality. For example, a beneficial effect may be a decrease in pain, a decrease in duration, frequency or intensity of crises, an increased hemocrit, an improved erythropoiesis, an increased reticulocyte count, an increased peripheral blood flow, a decreased hemolysis, decreased fatigue or an increased strength. Preferably, a therapeutic amount is that amount of chemical compound or agent that stimulates or enhances the expression of non-adult globin such as embryonic or fetal globin, or the proliferation of embryonic, fetal or adult globin expressing cells.

A blood disorder is any disease or malady which could be characterized as a direct or indirect consequence of a defect or disease of hemoglobin producing cells or the production of hemoglobin. The blood disorder may be associated with an anemia such as sickle cell anemia, hemolytic anemia, infectious anemia, aplastic anemias, hypoproliferative or hypoplastic anemias, sideroblastic anemias, myelophthisic anemias, antibody-mediated anemias, anemias due to enzyme-deficiencies or chronic diseases, anemias due to blood loss, radiation therapy or chemotherapy, thalassemias including α-like and β-like thalassemias, or globin disorders due to infections of viral, bacterial or parasitic origin such as malaria, trypanosomiasis, human immunodeficiency virus and other retroviruses, a polyoma virus such as JC virus, or a hepatitis virus such as human hepatitis vimses types A–G. Treatable blood disorders also include syndromes such as hemoglobin C, D and E disease, hemoglobin lepore disease, and HbH and HbS diseases. Treatment ameliorates one or more symptoms associated with the disorder. Symptoms typically associated with blood disorders include, for example, anemia, tissue hypoxia, organ dysfunction, abnormal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemolysis, jaundice, anemic crises and pain such as angina pectoris.

Compositions provided to the patient may include any combination of the proteins or chemical compounds of the invention or known to those of ordinary skill in the art. The patient may be a domesticated animal such as a dog, cat, horse, cow, steer, pig, sheep, goat or chicken, or a wild animal, but is preferably a human. Administration may be to an adult, an adolescent, a child, a neonate, an infant or in utero. Administration of the composition may be short term, continuous or sporadic as necessary. Patients with a suspected or diagnosed with a blood disorder may only require composition treatment for short periods of time or until symptoms have abated or have been effectively eliminated.

Compositions can be directly or indirectly administered to the patient. Indirect administration is performed, for example, by administering the composition to cells ex vivo and subsequently introducing the treated cells to the patient. The cells may be obtained from the patient to be treated or from a genetically related or unrelated patient. Related patients offer some advantage by lowering the immunogenic response to the cells to be introduced. For example, using techniques of antigen matching, immunologically compatible donors can be identified and utilized.

Direct administration of a composition may be by oral, parenteral, sublingual, rectal such as suppository or enteral administration, or by pulmonary absorption or topical application. Parenteral administration may be by intravenous injection, subcutaneous injection, intramuscular injection, intra-arterial injection, intrathecal injection, intra peritoneal injection or direct injection or other administration to one or more specific sites. Injectable forms of administration are sometimes preferred for maximal effect in, for example, bone marrow. When long term administration by injection is necessary, venous access devices such as medi-ports, in-dwelling catheters, or automatic pumping mechanisms are also preferred wherein direct and immediate access is provided to the arteries in and around the heart and other major organs and organ systems.

Another effective method of administering the composition is by transdermal transfusion such as with a dermal or cutaneous patch, by direct contact with, for example, bone marrow through an incision or some other artificial opening into the body. Compositions may also be administered to the nasal passages as a spray. Arteries of the nasal area provide a rapid and efficient access to the bloodstream and immediate access to the pulmonary system. Access to the gastrointestinal tract, which can also rapidly introduce substances to the blood stream, can be gained using oral enema, or injectable forms of administration. Compositions may be administered as a bolus injection or spray, or administered sequentially over time (episodically) such as every two, four, six or eight hours, every day (QD) or every other day (QOD), or over longer periods of time such as weeks to months. Compositions may also be administered in a timed-release fashion such as by using slow-release resins and other timed or delayed release materials and devices.

Orally active compositions are more preferred as oral administration is usually the safest, most convenient and economical mode of drug delivery. Oral administration is usually disadvantageous because compositions are poorly absorbed through the gastrointestinal lining. Compounds which are poorly absorbed tend to be highly polar. Consequently, compounds which are effective, as described herein, may be made orally bioavailable by reducing or eliminating their polarity. This can often be accomplished by formulating a composition with a complimentary reagent which neutralizes its polarity, or by modifying the compound with a neutralizing chemical group. Oral bioavailability is also a problem because drugs are exposed to the extremes of gastric pH and gastric enzymes. These problems can be overcome in a similar manner by modifying the molecular structure to withstand very low pH conditions and resist the enzymes of the gastric mucosa such as by neutralizing an ionic group, by covalently bonding an ionic interaction, or by stabilizing or removing a disulfide bond or other relatively labile bond.

Treatments to the patient may be therapeutic or prophylactic. Therapeutic treatment involves administration of one or more compositions of the invention to a patient suffering from one or more symptoms of the disorder. Symptoms typically associated with blood disorders include, for example, anemia, tissue hypoxia, organ dysfunction, abnormal hematocrit values, ineffective erythropoiesis, abnormal reticulocyte count, abnormal iron load, splenomegaly, hepatomegaly, impaired peripheral blood flow, dyspnea, increased hemolysis, jaundice, anemic crises and pain such as angina pectoris. Relief and even partial relief from one or more of these symptoms corresponds to an increased life span or simply an increased quality of life. Further, treatments that alleviate a pathological symptom can allow for other treatments to be administered.

Prophylactic treatments involve administration of a composition of the invention to a patient having a confirmed or suspected blood disorder without having any overt symptoms. For example, otherwise healthy patients who have been genetically screened and determined to be at high risk for the future development of a blood disorder may be administered compositions of the invention prophylactically. Administration can begin at birth and continue, if necessary, for life. Both prophylactic and therapeutic uses are readily acceptable because these compounds are generally safe and non-toxic.

Another embodiment of the invention is directed to a method for regulating the expression of a globin gene in a mammalian cell. Briefly, the cell is exposed to an effective amount of a composition of the invention. A poorly expressed or quiescent globin gene of the cell is stimulated to increase the expression of its protein product. An effective amount of the composition is that amount which increases the extent or magnitude of hematopoiesis, increases the proliferation of hemoglobin expressing cells, increases, decreases or balances expression from one or more globin genes, or increases or stimulates the specific expression of one or more globin genes such as an alpha ($\alpha$) globin gene, a zeta ($\xi$) globin gene, an epsilon ($\epsilon$) globin gene, a beta ($\beta$) globin gene, a delta ($\delta$) globin gene, a gamma (G-$\gamma$ or A-$\gamma$) globin gene, or an, at least, partly functional pseudo-globin gene. Cells can be treated in culture or in vivo. Cultures of treated cells will produce increased amounts of hemoglobin and preferably embryonic or fetal globin. This hemoglobin can be harvested for introduction to a patient or the stimulated cells themselves can be administered to the patient. Alternatively, recombinant cells containing a globin gene which can be stimulated by compositions of the invention can be utilized. These recombinant cells may be heterologous or homologous natural cells, or synthetically created cells such as a lipid vesicles.

Another embodiment of the invention is directed to a method for regulating the proliferation of hemoglobin expressing cells. As above, an effective amount of a composition of the invention is exposed to cells ex vivo or administered to cells in vivo. These cells or purified products harvested from these cells can be utilized to treat blood disorders by administration to patients. For example, increasing the amount of one or more different types of globin or hemoglobin expressing cells can alleviate symptoms associated with a blood disorder. Cells can be obtained from volunteers or the patients to be treated. Alternatively, treated cells or products derived from treated cells can be harvested, purified by, for example, column chromatography, and utilized for other medical applications such as diagnostic or other treatment monitoring screening kits.

Another embodiment of the invention is directed to a method for ameliorating a blood disorder by administering a therapeutically effective amount of a pharmaceutical composition containing an agent that stimulates the expression of a globin gene or stimulates the proliferation of hemoglobin expressing cells wherein the composition does not significantly decrease viability of the cell being treated or a normal cell. The therapeutically effective amount is that amount which ameliorates one or more symptoms of the blood disorder or reduces premature mortality. A normal cell is a relatively healthy mammalian cell that is not otherwise infected or transformed. Viability can be assayed by determining the effect of the composition on cell division, protein or nucleic acid synthesis, biochemical salvage pathways, amino acid or nucleotide transport processes, nucleic acid fragmentation or apoptosis and comparing the effects observed to control cells. Effects of the compositions can be tested in tissue culture or in vivo.

Patients with blood disorders are typically quite infirm with, for example, iron damaged organs and systems. Most treatments further tax the patient's already frail health in an effort to combat the disorder. This is true for both arginine butyrate and isobutyramide which decrease cell viability as determined in DNA fragmentation assays. To decrease cell viability is not necessary or desired for the treatment of blood disorders and may even be harmful. Surprisingly, many of the compositions of the invention maintain or, preferably, increase cell viability. This is a great benefit in the treatment of blood disorders and can significantly increase the chances for a successful outcome for the patient. For example, phenoxyacetic acid and butyric acid ethyl ester both reduce DNA fragmentation in fragmentation assays, and phenoxyacetic acid and $\alpha$-methyl cinnamic acid do not significantly alter system A transport of amino acids.

Another embodiment of the invention is directed to a method for increasing a hemoglobin content of blood comprising administering a composition to a patient containing a chemical compound of the structure: $R_1$—C(O)—$R_2$—$R_3$, phenyl—$R_5$—$R_6$—$R_7$ or phenyl—$R_9$—$R_{10}$ wherein; $R_1$=$SH_2$, $NH_2$ or OH; $R_2$=a branched or linear alkyl; $R_3$=$CONH_2$, $COSH_2$, COOH, $COOR_4$, C(O)$R_4$ or $OR_4$; $R_4$=a branched or linear alkyl; $R_5$=O, S or N; $R_6$=a branched or linear alkyl; $R_7$=COOH, $CONH_2$, $COSH_2$, $COOR_8$, C(O)$R_8$ or $OR_8$; $R_8$=a branched or linear alkyl; $R_9$=a branched alkyl of 2–4 carbon atoms or an unbranched alkyl of 2 or 4 carbon atoms; $R_{10}$=COOH, $CONH_2$, $COSH_2$, $COOR_{11}$, C(O)$R_{11}$ or $OR_{11}$; and $R_{11}$=a branched or linear alkyl. Hemoglobin content of blood so treated is increased greater than about 2%, preferably greater than about 5% and more preferably greater than about 10%. Patients which can be treated include any mammal such as a human. Chemical compounds which could be utilized include phenoxy acetic acid, butyric acid ethyl ester, cinnamic acid, hydrocinnamic acid, α-methyl hydrocinnamic acid, methyoxy acetic acid, phenyl butyric acid, thiophenoxy acetic acid, phenoxy propionic acid, succinamide, or a derivative or modification thereof. Such methods are useful to treat or prevent blood disorders in the same or a different patient. For example, to treat the same patient, the compound can be administered for a therapeutically effective period of time to allow the hemoglobin content of just the globin protein content to rise. Alternatively, the patient can be treated and the patient's blood collected at peak times of hemoglobin or globin production, collected and stored, and administered to another patient or re-administered to the same patient. Such treatments would be useful therapies for those being treated with radiation therapy, chemotherapy, bone marrow transplants, blood diseases, such as sickle cell disease and thalassemia, and other disorders which would be alleviated with an increased blood hemoglobin content.

Another embodiment of the invention is directed to specific transcription factors which directly or indirectly control or affect expression of one or more genes of the alpha or beta globin gene clusters. Factors may be activators or repressors of transcription or translation and can be purified from mammalian cells, organically synthesized or recombinantly expressed. Factors may contain the entire amino acid sequence of the protein or only active portions or subunits thereof. Nucleic acid sequences which encode these transcription factors can be identified and cloned into plasmids, cosmids, viral vectors or phage vectors and expressed as, for example, protein or anti-sense RNA. Specific binding sites of the above transcription factors may also be cloned and the sequences used to effect gene specific expression or used in a competitive manner to control activity of the factors to which they bind. Control may also be exercised by administering polyclonal or monoclonal antibodies specific to a factor. Factor-specific antibodies may be useful for the treatment or prevention of blood disorders by selectively removing transcription factors from a patient's system which inhibit or suppress globin expression or by binding to cell surface markers which effect factor activity.

Another embodiment of the invention is directed to methods for the treatment of a patient with an infection or a neoplastic disorder. Treatable infectious diseases include bacterial infections such as sepsis and pneumonia, infections caused by bacterial pathogens such as, for example, Pneumococci, Streptococci, Staphylococci, Neisseria, Chlamydia, Mycobacteria, Actinomycetes and the enteric microorganisms such as enteric Bacilli; viral infections caused by, for example, a hepatitis virus, a retrovirus such as HIV, an influenza virus, a papilloma virus, a herpes virus (HSV I, HSV II, EBV), a polyoma virus, a slow virus, paramyxovirus and corona virus; parasitic diseases such as, for example, malaria, trypanosomiasis, leishmania, amebiasis, toxoplasmosis, sarcocystis, pneumocystis, schistosomiasis and elephantitis; and fungal infections such as candidiasis, phaeohyphomycosis, aspergillosis, mucormycosis, cryptococcosis, blastomycosis, paracoccidiodomycosis, coccidioidomycosis, histomycosis, actinomycosis, nocardiosis and the Dematiaceous fungal infections.

Anti-neoplastic activity includes, for example, the ability to induce the differentiation of transformed cells including cells which comprise leukemias, lymphomas, sarcomas, neural cell tumors, carcinomas including the squamous cell carcinomas, seminomas, melanomas, neuroblastomas, mixed cell tumors, germ cell tumors, undifferentiated tumors, neoplasm due to infection (eg. viral infections such as a human papilloma virus, herpes viruses including Herpes Simplex virus type I or II or Epstein-Barr virus, a hepatitis virus, a human T cell leukemia virus (HTLV) or another retrovirus) and other malignancies. Upon differentiation, these cells lose their aggressive nature, no longer metastasize, are no longer proliferating and eventually die and/or are removed by the T cells, natural killer cells and macrophages of the patient's immune system. The process of cellular differentiation is stimulated or turned on by, for example, the stimulation and/or inhibition of gene specific transcription. Certain gene products are directly involved in cellular differentiation and can transform an actively dividing cell into a cell which has lost or has a decreased ability to proliferate. An associated change of the pattern of cellular gene expression can be observed. To control this process includes the ability to reverse a malignancy. Genes whose transcriptional regulation are altered in the presence of compositions of the invention include the oncogenes myc, ras, myb, jun, abl and src. The activities of these gene products as well as the activities of other oncogenes are described in J. D. Slamon et al. (Science 224:256–62, 1984).

Another example of anti-neoplastic activity includes the ability to regulate the life cycle of the cell, the ability to repress angiogenesis or tissue regeneration through the blockade or suppression of factor activity, production or release, the ability to regulate transcription or translation, or the ability to modulate transcription of genes under angiogenesis, growth factor or hormonal control. These activities are an effective therapy particularly against prostatic neoplasia and breast carcinomas. Additional anti-neoplastic activities include the ability to regulate the cell cycle for example by effecting time in and passage through S phase, M phase, $G_1$ phase or $G_0$ phase, the ability to increase intracellular cAMP levels, the ability to inhibit or stimulate histone acetylation, the ability to methylate nucleic acids and the ability to maintain or increase intracellular concentrations of anti-neoplastic agents.

The neoplastic disorder may be any disease or malady which could be characterized as a neoplasm, a tumor, a malignancy, a cancer or a disease which results in a relatively autonomous growth of cells. Neoplastic disorders prophylactically or therapeutically treatable with compositions of the invention include small cell lung cancers and other lung cancers, rhabdomyosarcomas, chorio carcinomas, glioblastoma multiformas (brain tumors), bowel and gastric carcinomas, leukemias, ovarian cancers, prostate cancers, osteosarcomas or cancers which have metastasized. Diseases of the immune system which are treatable by these compositions include the non-Hodgkin's lymphomas including the follicular lymphomas, Burkitt's lymphoma, adult T-cell leukemias and lymphomas, hairy-cell leukemia, acute myelogenous, lymphoblastic or other leukemias, chronic myelogenous leukemia, and myelodysplastic syndromes. Additional diseases treatable by the compositions include virally-induced cancers wherein the viral agent is EBV, HPV, HTLV-1 or HBV, breast cell carcinomas, melanomas and hematologic melanomas, ovarian cancers, pancreatic cancers, liver cancers, stomach cancers, colon cancers, bone cancers, squamous cell carcinomas, neurofibromas, testicular cell carcinomas and adenocarcinomas.

In another embodiment of the invention, compositions of the invention may be used in combination with other antineoplastic agents or therapies to maximize the effect of the compositions in an additive or synergistic manner. Cytokines which may be effective in combination with the compositions of the invention include growth factors such as B cell growth factor (BCGF), fibroblast-derived growth factor (FDGF), granulocyte/macrophage colony stimulating factor (GM-CSF), granulocyte colony stimulating factor (G-CSF), macrophage colony stimulating factor (M-CSF), epidermal growth factor (EGF), platelet derived growth factor (PDGF) nerve growth factor (NGF), stem cell factor (SCF), and transforming growth factor (TGF). These growth factors plus a composition may further stimulate cellular differentiation and/or the expression of certain MHC antigens or tumor specific antigens. For example, BCGF plus a composition may be effective in treating certain B cell leukemias. NGF plus a composition may be useful in treating certain neuroblastomas and/or nerve cell tumors. In a similar fashion, other agents such as differentiating agents may be useful in combination with a composition of the invention to prevent or treat a neoplastic disorder. Other differentiating agents include B cell differentiating factor (BCDF), erythropoietin (EPO), steel factor, activin, inhibin, the bone morphogenic proteins (BMPs), retinoic acid or retinoic acid derivatives such as retinol, the prostaglandins, and TPA.

Alternatively, other cytokines and related antigens in combination with a composition may also be useful to treat or prevent neoplasia. Potentially useful cytokines include tumor necrosis factor (TNF), the interleukins (IL-1, IL-2, IL-3, etc.), the interferon proteins (IFN) IFN-$\alpha$, IFN-$\beta$, and IFN-$\gamma$, cyclic AMP including dibutyryl cyclic AMP, hemin, hydroxyurea, hypoxanthine, glucocorticoid hormones, dimethyl sulfoxide (DMSO), and cytosine arabinoside, and anti-virals such as acyclovir and gemciclovirs. Therapies using combinations of these agents would be safe and effective against malignancies and other forms of cancer. Combinations of therapies may also be effective in inducing regression or elimination of a tumor or some other form of cancer such as compositions of the invention plus radiation therapy, toxin or drug conjugated antibody therapy using monoclonal or polyclonal antibodies directed against the transformed cells, gene therapy or specific anti-sense therapy. Effects may be additive, logarithmic, or synergistic, and methods involving combinations of therapies may be simultaneous protocols, intermittent protocols or protocols which are empirically determined.

Another embodiment of the invention comprises compositions and methods for the treatment of neoplastic disorders by augmenting conventional chemotherapy, radiation therapy, antibody therapy, and other forms of therapy. Compositions containing chemical compounds of the invention, in combination with chemotherapeutic agents, enhance the effect of the chemotherapeutic agent alone. Compositions decrease the expression or activity of proteins responsible for lowering the intra-cellular concentration of chemotherapeutic agents. Proteins responsible for resistance to drugs and other agents, the multi-drug resistance (MDR) proteins, include the P-glycoprotein (Pgp) encoded by the mdr-1 gene. Consequently, conventional drugs for the treatment of neoplastic disorders accumulate at higher concentrations for longer periods of time and are more effective when used in combination with the compositions herein. Some conventional chemotherapeutic agents which would be useful in combination therapy with compositions of the invention include the cyclophosphamide such as alkylating agents, the purine and pyrimidine analogs such as mercapto-purine, the vinca and vinca-like alkaloids, the etoposides or etoposide like drugs, the antibiotics such as deoxyrubocin and bleomycin, the corticosteroids, the mutagens such as the nitrosoureas, antimetabolites including methotrexate, the platinum based cytotoxic drugs, the hormonal antagonists such as antiinsulin and antiandrogen, the antiestrogens such as tamoxifen an other agents such as doxorubicin, L-asparaginase, dacarbazine (DTIC), amsacrine (mAMSA), procarbazine, hexamethylmelamine, and mitoxantrone. The chemotherapeutic agent could be given simultaneously with the compounds of the invention or alternately as defined by a protocol designed to maximize drug effectiveness, but minimize toxicity to the patient's body.

Another embodiment of the invention is directed to aids for the treatment of human disorders such as infections, neoplastic disorders and blood disorders. Aids contain compositions of the invention in predetermined amounts which can be individualized in concentration or dose for a particular patient. Compositions, which may be liquids or solids, are placed into reservoirs or temporary storage areas within the aid. At predetermined intervals, a set amount of one or more compositions are administered to the patient. Compositions to be injected may be administered through, for example, mediports or in-dwelling catheters. Aids may further comprise mechanical controls or electrical controls devices, such as a programmable computer or computer chip, to regulate the quantity or frequency of administration to patients. Examples include the Baxa Dual Rate Infuser (Baxa Corp.; Englewood, Colo.) and the Baxa Programmable Infuser (Baxa Corp.; Englewood, Colo.). Delivery of the composition may also be continuous for a set period of time. Aids may be fixed or portable, allowing the patient as much freedom as possible.

The following examples are offered to illustrate embodiment of the present invention, but should not be viewed as limiting the scope of the invention

EXAMPLES

Example 1

Stimulation of Erythroid Proliferation in Cell Cultures

Peripheral blood was collected from normal volunteers and patients with anemia due to sickle cell disease or thalassemia Mononuclear cells were isolated by Ficoll-Hypaque (Pharmacia Biotech; Piscataway, N.J.) centrifugation and cultured in Iscove's Modified Dulbecco's Media (IMDM; GIBCO/BRL; Grand Island, N.Y.) supplemented with 10% fetal calf serum, 300 $\mu$g/ml glutamine, 3 units/ml IL 3 (Amgen; Thousand Oaks, Calif.), and 2 units/ml erythropoietin (Terry Fox Labs; Vancouver, B.C.). Chemical compounds were obtained from Sigma Chemical (St. Louis, Mo.) or Aldrich Chemical (Milwaukee, Wis.), unless otherwise indicated, and formulated into pharmaceutical compositions by dissolving in aqueous solutions of media or sterile water pH adjusted to about 7.4. Solutions were sterilized by passage at least once through 0.22 micron Nalgene filters and added to cell cultures at final concentrations that are pharmaceutically achievable in vivo (typically between about 0.1 mM to 2.0 MM). Cells were incubated with compounds for between 13–14 days at 37° C. in humidified 5% $CO_2$, and fed and passed, as necessary. Colony growth, proportion of fetal globin-expressing cells and amounts of fetal globin production were assayed. Results are presented in Table 1 as BFU-e stimulation (colony growth).

TABLE 1

Stimulation of Erythrocyte Proliferation

| Treatment | Concentration | BFU-e Stimulation |
| --- | --- | --- |
| Untreated Cells | — | — |
| DHC | 0.1 mM | 124% |
| PAA | 0.1 mM | 135% |

Dihydrocinnamic acid (DHC) at 0.1 mM produced 124% more BFU-e (burst forming unit-erythroid) colonies from the same number of mononuclear cells than the control cultures. Phenoxyacetic acid (PAA) at 0.1 mM produced 135% more BFU-e colonies from the same number of mononuclear cells than the control cultures. BFU-e are the largest erythroid progenitor population, with each colony producing from 5,000 to 10,000 red blood cells. This degree of stimulation would produce at least about 24% and 35% more red blood cells in vivo.

Example 2
Erythroid Cell Viability After Stimulation

Figure 2:
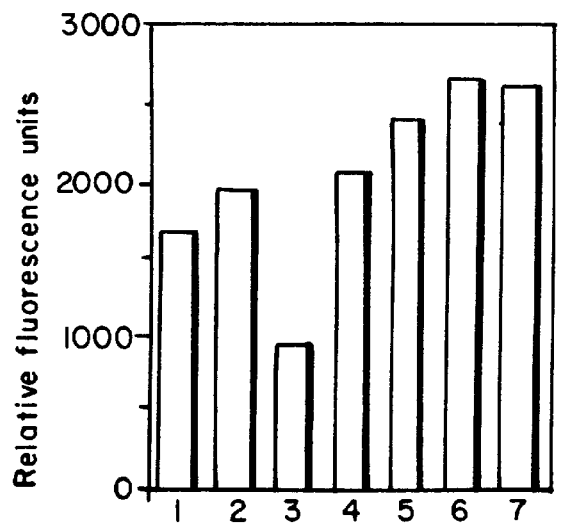
FIG. 2 Peripheral blood cell viability after incubation with arginine butyrate, dihydrocinnamic acid, phenoxyacetic acid and butyric acid ethyl ester.

Compositions were tested for the ability to directly stimulate erythroid cell growth. Cell growth stimulation is a useful property for an agent to be used to treat anemias and distinguishes such agents from the cytotoxic drugs currently being tested for treatment of hemoglobinopathies. Cell viability analyses were performed using fluorescent staining to detect living cells. Cells were in log phase of growth in 6-well dishes when used in proliferation assays. For enumeration of living cells, wells were washed once with medium to remove nonadherent or dead cells. Remaining live cells were labeled with 2 $\mu$M 2',7'-bis-(carboxyethyl)-5-(and 6)-carboxy-fluorescein acetoxy-methyl ester (Calcein-AM) (Molecular Probes; Eugene, Oreg.) for 20 minutes at 37° C. and washed once. Fluorescence intensity of live cells was read on a CytoFluor 2300 Fluorescence Plate Scanner (Millipore; Bedford, Mass.) at excitation and emission wavelengths of 485 and 530 nm, respectively. The fluorescence intensity of a well was proportional to the number of living cells in the well. Background fluorescence was measured separately for each plate and subtracted from all readings. Each experiment was performed in triplicate or quadruplicate. The standard deviation (SD) of repetitive readings was less than 30% of the mean. Results are depicted in FIG. 2. In contrast to arginine butyrate (lane 2=AB at 0.2 mM; lane 3=AB at 0.5 mM), which inhibited proliferation compared to untreated controls (lane 1), isobutyramide (lane 4=IBT at 0.5 mM), dihydrocinnamic acid (lane 5=DHC at 0.5 mM), phenoxyacetic acid (lane 6=PAA at 0.5 mM), and butyric acid ethyl ester (lane 7=BAEE at 0.5 mM) either had no effect or stimulated erythroid cell growth and proliferation.

Figure 3A:
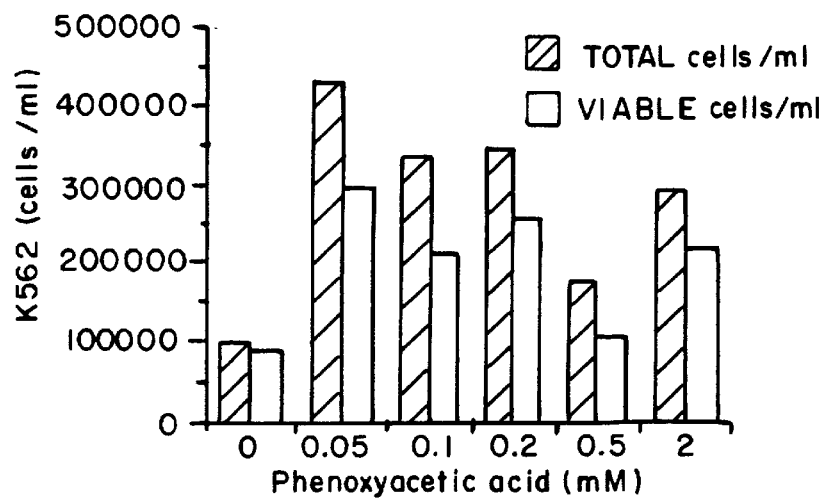
FIG. 3 Cell viability as determined by the comparative numbers of total and viable K562 cells in the presence of increasing concentrations of (A) phenoxyacetic acid, (B) dihydrocinnamic acid, (C) butyric acid ethyl ester, (D) arginine butyrate, and (E) isobutyramide.
Figure 3B:
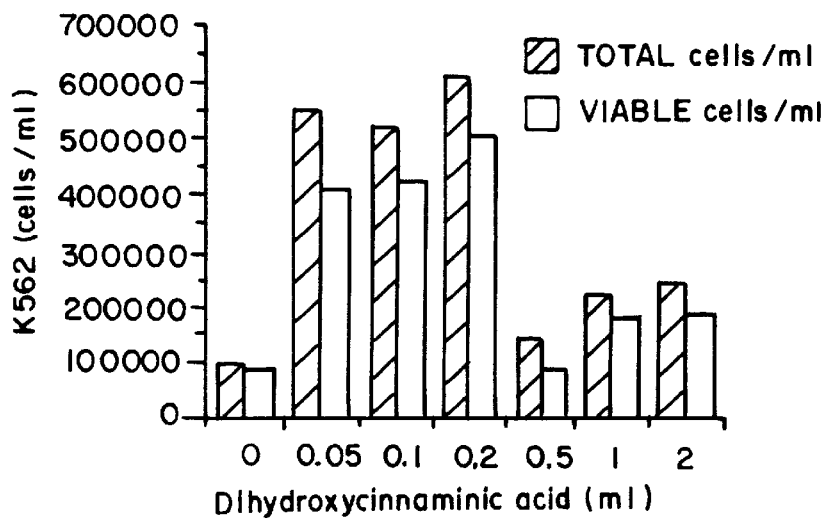
Figure 3C:
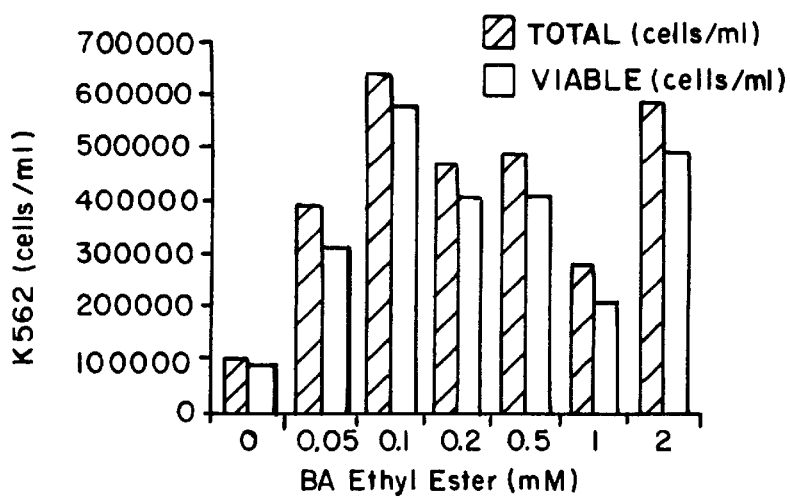
Figure 3D:
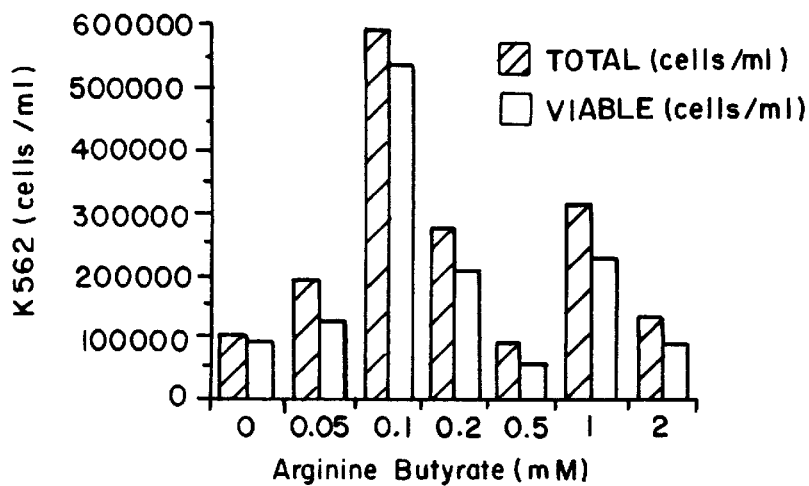
Figure 3E:
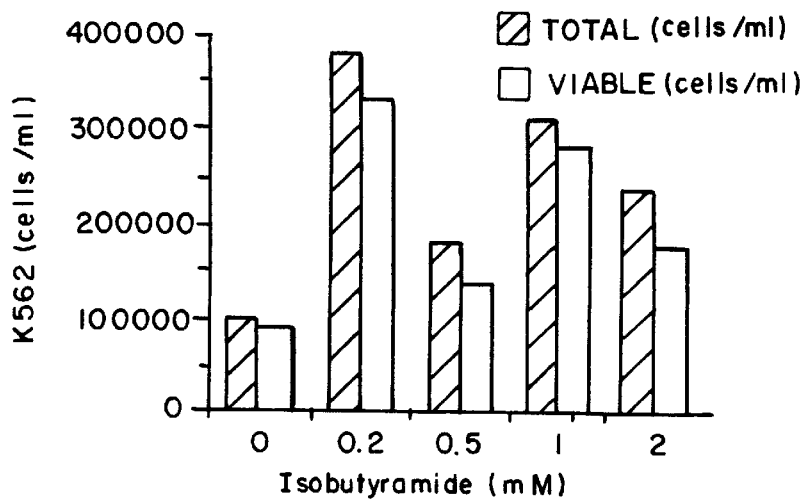

Dose response curves at dosages of up to 2.0 mM were also determined for phenoxyacetic acid (PAA; FIG. 3A), dihydrocinnamic acid (DHC; FIG. 3B), butyric acid ethyl ester (BAEE; FIG. 3C), arginine butyrate (AB; FIG. 3D) and isobutyramide (IBT; FIG. 3E). Cells were counted on day 4 of treatment and viable cells identified by trypan blue exclusion. In contrast to arginine butyrate, wherein concentrations above 0.2 mM suppressed cell growth, BAEE and PAA did not significantly inhibit proliferation at up to 2.0 mM concentrations.

Example 3
Fetal Globin Expression in Human Cell Cultures

Compositions were tested for activity in inducing fetal globin expression and protein production in erythroid progenitor cells cultured from human cord blood and analyzed as described by S. P. Perrine et al. (Blood 74: 454–60, 1989). Briefly, mononuclear cells were cultured in IMDM with 30% fetal calf serum and 2 units erythropoietin per ml to induce erythroid differentiation. Colonies were harvested on day 12–13, incubated with radio-labelled ($^3$H) leucine, and further incubated in leucine-free media, still in the presence of compounds, overnight. Globin composition in the erythroid cells was analyzed by laser densitometry of electrophoretically separated globin chains stained with Coomassie blue, and by autoradiography. Treated cells were incubated for 12–13 days (Table 2, Experiments A and B) or overnight (Table 2, Experiment C) in the presence of the indicated compounds and compared to untreated control cells cultured from the same human subject.

TABLE 2

Stimulation of Fetal Globin Expression

| Treatment | Conc. | Gamma/(Gamma + Beta) | Gamma Increase |
| --- | --- | --- | --- |
| Exp. A: | | | |
| Untreated | — | 76.0% | — |
| PAA | 0.1 mM | 82.0% | 6.0% |
| DHC | 0.1 mM | 88.0% | 12.0% |
| BAEE | 0.1 mM | 89.5% | 13.0% |
| Exp. B: | | | |
| Untreated | — | 25.4% | — |
| Untreated | — | 27.5% | — |
| PAA | 0.5 mM | 38.8% | 13.0% |
| BAEE | 0.2 mM | 74.0% | 8.5% |
| MHPP | 0.05 mM | 29.8% | 2.0% |
| | 1.0 mM | 24.0% | −3.5% |
| Exp. C: | | | |
| Untreated | — | 52.0% | — |
| PAA | 0.5 mM | 55.6% | 3.6% |
| DHC | 0.1 mM | 76.0% | 24.0% |
| | 0.2 mM | 71.9% | 20.0% |
| | 0.5 mM | 71.3% | 19.0% |
| BAEE | 0.1 mM | 64.6% | 12.5% |

Figure 4:
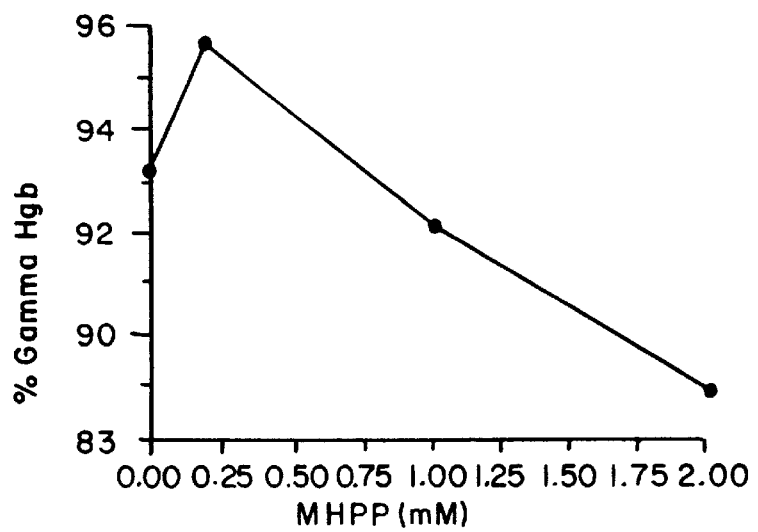
FIG. 4 Percent gamma globin synthesis in the presence of increasing concentrations of the isobutyramide metabolite, 2-methyl-3-hydroxy propionamide.

In the first test, cells cultured in the presence of 0.1 dihydrocinnamic acid (DHC) or 0.1 mM butyric acid ethyl ester (BAEE) produced an increase in fetal globin protein of 12.0% and 13.0%, respectively, above untreated cells from the same subject. Cells treated with 0.1 mM phenoxyacetic acid (PAA) induced an increase of 6% fetal globin protein over untreated cells. In a second experiment, treatment with 0.5 mM phenoxyacetic acid induced a 13% increase in fetal globin protein, and treatment with 0.2 mM butyric acid ethyl ester (BAEE) induced an increase of 8.5% more fetal globin protein than untreated controls. A related compound, a metabolite of isobutyramide, 2 methyl-3-hydroxypropionamide (MHPP), decreased the expression of fetal globin in similarly cultured cells at concentrations above 0.25 mM (FIG. 4). This same composition, increased fetal globin expression when used at concentrations below 0.25 mM. In a third experiment, results for the most part were even more pronounced. Dihydrocinnamic acid (DHC)

increased expression 24% at 0.1 mM, 20% at 0.2 mM, and 19% at 0.5 mM, phenoxyacetic acid increased expression 3.6% at 0.5 mM, and butyric acid ethyl ester increased fetal globin expression 12.5%.

Example 4
Stimulation of Fetal Globin mRNA in Erythroleukemia Cells

Compounds were tested for increased expression of the human globin genes in human erythroid cells. In addition, as the cell line being tested is a tumor cell line, the assay determines if differentiation, a growth inhibitory effect on cancer cells, is induced by the compounds tested. Human erythroleukemia cells were cultured in RPMI media with 10% fetal calf serum alone or with treatment with various compounds for 4 days. Globin MRNA was quantitated by primer extension analysis. Fetal globin mRNA was compared to the amount of fetal globin mRNA produced in untreated cells during the same culture period. The quantitation was expressed as a percent of alpha globin MRNA which was constant. Results are expressed proportional to α-globin mRNA (Table 3).

TABLE 3

Stimulation of Fetal Globin mRNA Expression

| Treatment | Concentration | Gamma/Alpha | Gamma Globin mRNA |
|---|---|---|---|
| Untreated | — | 0.46 | — |
| AB | 1.0 mM | 0.66 | 20% ↑ |
| MB | 1.0 mM | 0.73 | 26% ↑ |
| PAA | 1.0 mM | 0.70 | 24% ↑ |
| BAEE | 1.0 mM | 0.90 | 44% ↑ |

As shown, AB, MB, PAA and BAEE all significantly increased the induction of fetal globin MRNA in human cells. Surprisingly, BAEE stimulated fetal globin expression 44% which is over two times greater than even AB alone. Increases in fetal globin synthesis of even 1–3% are significant because even small increases in synthesis of fetal globin protein have been shown to ameliorate the symptoms and decrease early mortality of sickle cell disease (O. S. Platt et al., N. Engl. J. Med. 330:1639–44, 1994; S. Karlsson et al., Ann. Rev. Biochem. 54:1071–108, 1985; W. G. Wood et al., Brit. J. Haematol. 45:431–45, 1980).

Induction of globin MRNA expression is also a marker for differentiation in these tumor cells. Gamma globin MRNA increased from 46% to 90%. Therefore, these compounds also induce differentiation of this cancer cell line into a more mature phenotype indicating a utility against many types of neoplasms.

Example 5
Induction of Fetal Globin in Erythroblasts by Steel Factor

Figure 5A:
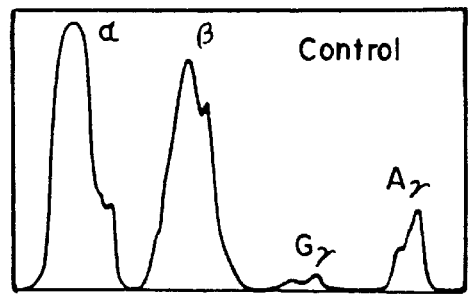
FIG. 5 Histogram of the amounts and forms of globin synthesized in peripheral blood BFU-e's (A) before and (B) after treatment with steel factor.
Figure 5B:
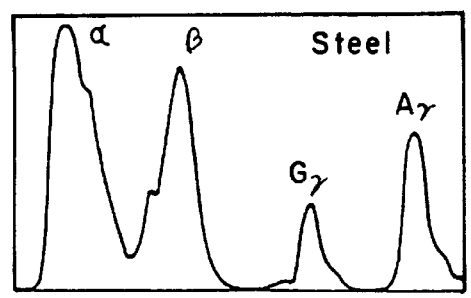

Peripheral blood was obtained from patients with sickle cell anemia. Mononuclear cells were isolated on Ficoll-Hypaque gradients. One culture was treated with 100 ng/ml steel factor for 13 days and compared with an untreated control. Gamma globin expression showed a mean increase of 16.1% in the treated erythroblast culture. A second culture was incubated overnight with an identical dose of steel factor plus $^3$H-leucine. Amounts of labeled globin proteins synthesized in untreated (FIG. 5A) and steel factor treated (FIG. 5B) cells were determined by autoradiography and quantitated (scanned) by laser densitometry. Gamma globin expression increased from 17.6% to 43.3%. The increase observed included both G-γ and A-γ globin proteins. BFU-e cells from this same patient cultured for 13 days with steel factor at 100 ng/ml showed a surprisingly dramatic increased gamma globin expression from 14% to 23.3% in a very short time.

Example 6
Assays of Cell Viability and DNA Integrity

Compounds were tested for their ability to induce DNA fragmentation, an indicator of apoptosis or programmed cell death, or to decrease cell viability at high concentrations, similar to those which might be reached in vivo. Such activities might limit their utility for treatment of anemias such as occur in thalassemia, but alternatively would be useful for anticancer effects. To determine cell viability, human erythroid cells were cultured in the presence and absence of these compounds for 4 days and the amount of DNA fragmentation which occurred was measured.

Cell viability analyses were performed using fluorescent staining to detect living cells. Cells were in log phase of growth in 6-well dishes when used in proliferation assays. For enumeration of living cells, wells were washed once with medium to remove nonadherent or dead cells. Remaining live cells were labeled with Calcein-AM for 20 minutes at 37° C. and washed once. Fluorescence intensity of adherent live cells was read on a CytoFluor 2300 Fluorescence Plate Scanner (Millipore; Bedford, Mass.) at excitation and emission wavelengths of 485 and 530 nm, respectively. The fluorescence intensity of a well was proportional to the number of living cells in the well. Background fluorescence was measured separately for each plate and subtracted from all readings. Each experiment was performed in triplicate or quadruplicate. The standard deviation (SD) of repetitive readings was less than 30% of the mean.

Arginine Butyrate (AB) at 0.2 mM, dihydrocinnamic acid (DHC) at 0.5 mM, phenoxy acetic acid (PAA) at 0.5 mM, and butyric acid ethyl ester (BAEE) at 0.5 mM, either did not inhibit, or slightly enhanced growth of the human erythroid cell line K562 over 3 days. At higher concentrations, still easily achievable in vivo, arginine butyrate (0.5 mM) and dihydrocinnamic acid (greater than 0.5 mM) inhibited growth of this tumor cell line by approximately 50%. Therefore, these compounds are also useful as anti-tumor agents.

Flow cytometric determination of DNA profiles and DNA fragmentation were determined. Cytometric analysis was performed with a FACScan (Becton Dickenson Instruments; Columbia, Md.). The data analysis and display were performed using the Cell-Fit software program. Approximately $0.5 \times 10^6$ cells were washed twice with PBS and resuspended in 1 ml of 1% sodium citrate, 0.1% Triton X-100 and 50 μg of propidium iodide/ml. Resulting permeabilized cells were kept in the dark at 4° C. overnight before DNA profile or DNA fragmentation analysis (Table 4).

TABLE 4

| | Degradation of DNA | |
|---|---|---|
| Treatment | Concentration | Degraded DNA |
| Control | — | 26% |
| Control | — | 22% |
| AB | 0.5 mM | 32% |
| AB | 1.0 mM | 34% |
| AB | 2.0 mM | 44% |
| IBT | 2.0 mM | 34% |
| PAA | 2.0 mM | 20.6% |
| BAEE | 2.0 mM | 13.8% |

Arginine butyrate and isobutyramide at 1.0 mM to 2.0 mM concentrations produced an increase in degraded DNA (44%), while treatment with butyric acid ethyl ester and phenoxyacetic acid at 1.0 mM to 2.0 mM concentrations, respectively, resulted in a lower proportion of degraded DNA (13.8% and 20.6%) than was observed even in untreated cells (26%). These assays indicate that these compounds do not adversely affect DNA integrity at the indicated doses. As patients with blood disorders are generally of poor health, wherein the defective blood cells produced often prematurely degrade their DNA, treatments which do not further cause increased cell death or that actually promote red blood cell viability would be extremely clinically advantageous.

Example 7
Induction of Fetal Globin Gene Promoter Activity in Transfected Cells

Gamma globin promoter-neomycin transfection experiments were performed to determine if compounds act by inducing an increase in activity from the proximal promoter of the gamma globin gene. Constructs containing 61 bp of the proximal gamma globin promoter were linked to the reporter gene for neomycin phosphotransferase (NEO) and transfected into permissive K562 cells by electroporation. After 18 hours, transfected cells were passed at $10^3$ cells per well into RPMI media containing G418 (neomycin), which kills all mammalian cells unless the gene for NEO is expressed. Phenoxyacetic acid and thiophenoxyacetic acid were added to some of the cells plated into the RPMI/G418 media at concentrations of 1 mM. Cultures were incubated for 8 weeks with media changes performed as needed. Colonies which survived and grew in the presence of G418 were scored and the number of such colonies was compared to those generated when the cells were plated into G418 media without the test compounds. No colonies in the 24 wells survived in the absence of compounds. There was a greater than 6-fold (>600%) increase in proportions of colonies surviving the presence of phenoxyacetic acid (6/24 wells) and a three-fold (300%) increase in survival in the presence of thiophenoxyacetic acid (3/24 wells). These results demonstrate that these compounds (phenylalkyl acids) stimulate activity from the proximal promoter of the human fetal globin gene.

Example 8
Elevation of Hemoglobin Levels Without Inducing Fetal Globin

Experiments were performed to demonstrate that isobutyramide can increase total red blood cell counts and total hemoglobin levels in a patient with thalassemia (18 year old male with thalassemia intermedia) without affecting fetal globin levels. This patient received isobutyramide at 50 mg/kg for 3 days/week over the course of the study. Results are shown in Table 5.

TABLE 5

Induction in Red Blood Cell Production

| Date | RBC | Hgb | Hct | Retics | Hgb-A1 | Hgb-A2 | HbF |
|---|---|---|---|---|---|---|---|
| Day 1 | 6.48 | 10.1 | 31.1 | 1.7 | 89.2 | 6.4 | 4.4 |
| Day 8 | 6.76 | 10.8 | 36.2 | 2.5 | 89.2 | 6.2 | 6.4 |
| Day 15 | 6.89 | 11.1 | 37.0 | 1.8 | 89.2 | 6.4 | 4.4 |
| Day 22 | 6.28 | 10.3 | 34.1 | 2.0 | 89.1 | 6.9 | 0.4 |
| Day 29 | 6.61 | 10.9 | 36.3 | 2.0 | 88.6 | 7.0 | 4.4 |
| Day 36 | 6.28 | 10.4 | 33.8 | 1.6 | 88.4 | 7.6 | 0.4 |
| Day 43 | 6.38 | 11.0 | 36.2 | 2.0 | 88.7 | 6.5 | 8.4 |
| Day 55 | 6.68 | 11.4 | 34.0 | 2.8 | | | 5.4 |
| Day 68 | 6.68 | 11.5 | 36.4 | 2.4 | | | 1.4 |
| Day 96 | 7.33 | 11.7 | 36.9 | 2.5 | | | |

Figure 6:
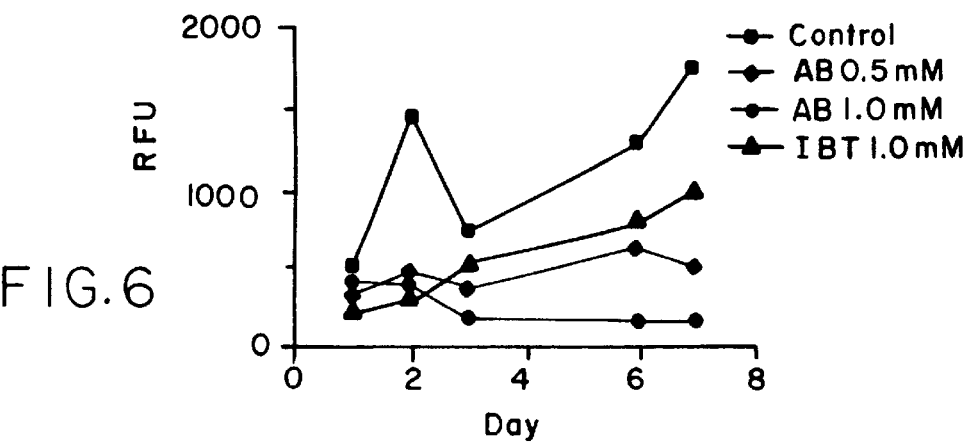
FIG. 6 MCF-7 cell viability determined by fluorescent analysis after incubation with arginine butyrate and isobutyramide.

Hemoglobin-A1 and hemoglobin-A2 levels were approximately constant throughout the study. Hemoglobin (Hgb) rose 1.6 g/dl (from 10.1 to 11.7 g/dl), hematocrit (Hct) rose 5.8% (from 31.0% to 36.9%), reticulocytes (Retics) rose about 50% (1.7 to $2.5 \times 10^6$ cells), and total red blood cells (RBC) rose by almost $10^6/\mu l$ (6.48 to $7.3 \times 10^6$ cells/$\mu l$) over the four month study period despite the lack of increased fetal globin (HbF). This compound has a salubrious effect on red blood cell and hemoglobin production independent of induction of fetal globin Example 9
Effects of Compounds on Human Mammary Carcinoma Cells Human mammary carcinoma cells (MCF-7) were cultured alone (controls) and with arginine butyrate or isobutyramide for 4 days. Viability was assayed by FACS after incubation with a fluorescent dye taken up by viable cells (FIG. 6). Growth was decreased by 50% with isobutyramide at 1.0 mM, about 60% with arginine butyrate at 0.5 mM, and greater than 90% with arginine butyrate at 1.0 mM.

Example 10
Induction of In Vivo Reticulocyte Proliferation and Globin Expression Experiments were performed to determine if administration of the chemical compositions could induce fetal globin gene expression in an in vivo model similar to humans (S. P. Perrine et al., Brit. J. Haematol. 88:555–61, 1994). Briefly, chemicals were prepared as sterile pharmaceutical solutions in pH adjusted sterile water. A variety of chemical compositions were administered sequentially to some baboons. After administration of one compound, a wash-out period with no compound administration was maintained until reticulocytes returned to base line prior to administration of the next compound. This was done, at least partly, to compare the magnitude of response which occurred within the same individual animal to different compounds.

Briefly, juvenile female baboons (2 years old) were catheterized with arterial and venous catheters and phlebotomized gradually every day to maintain a moderate anemia of 7.0 to 7.5 grams hemoglobin/dl. Fetal reticulocytes, the newly produced red blood cells containing fetal globin, were assayed using a monoclonal antibody against fetal globin (HbF) as described by G. Dover et al. (Blood 67:735–38, 1986). Briefly, blood was stained with two antibodies, one specific for reticulocytes and another against fetal globin protein. The amount of antibody bound cells was determined by FACS analysis. Globin chain synthesis was assayed as described by J. B. Clegg et al. (J. Mol. Biol. 19:91–108, 1966). Briefly, reticulocytes were radio-labeled with $^3$H-leucine which was incorporated in equal proportions into actively synthesized globin chains. After incubation in leucine-free media, cells were washed, and globin proteins were separated and purified by column chromatography. Radioactivity incorporated into each peak is compared and the ratios of gamma to gamma plus beta globin calculated. Each animal served as its own control with baseline monitoring assays performed for 4–6 weeks before any drug was administered. Phlebotomy was continued daily, so that peripheral HbF levels in the animals were not considered to be accurate over the short treatment time-frames and were not monitored. Safety monitoring was performed by frequent physical examinations, quantitation of food eaten, activity and frequent chemistry and hematology monitoring. Complete blood counts were assayed before, during and after treatment. Results presented were not adjusted to account for the daily phlebotomy.

A pharmaceutical composition of α-methyl hydrocinnamic acid was infused each day for 5 days over an 8 hour period at a dose of 500 mg/kg for 2 days, 700 mg/kg for 2 days and 1,000 mg/kg for 1 day. With treatment, total hemoglobin rose by 1.5 grams/dl over 3 days from 6.4 to 7.9 grams/dl and despite continued daily phlebotomy. Packed red blood cell volume rose from 19.5% to 31.2% of total blood volume and red blood cell count rose from 2.28 to $3.53 \times 10^6$ red blood cells per microliter. White blood cell count rose from 4.1 to $11.5 \times 10^6$ cells/$\mu$l and platelet count rose from 26.7 to $46.8 \times 10^4$ cells/$\mu$l of blood. The total number of reticulocytes, the proportion of newly produced red blood cells, rose from 5.6% to 11% after treatment. These increases in all types of blood cell counts demonstrates that these compounds increase growth of all blood cell lineages.

A second baboon was treated with pharmaceutical composition of $\alpha$-methyl hydrocinnamic acid at 500 mg/kg for 8 hours, at 700 mg/kg for 8 hours, and again at 700 mg/kg for 2, 4 and 6 hours. Total fetal globin synthesis increased from 4.0% to 10.8% after 5 days. Blood counts increased over the same 5 day period despite the daily withdrawal of 5% blood volume. White blood cell counts increased from 8,700 to a maximum of 14,300. Red blood cell counts increased from $2.3 \times 10^6$ to $2.82 \times 10^6$. Packed red blood cell volume rose from 14.5% to 20.2% and platelet counts rose from 328,000 to a high of 486,000. Total hemoglobin rose by 1.4 grams from 4.6 to 6.0 g/dl. These responses indicate that the compound, in a very short time, stimulated production of many different cell types.

A pharmaceutical composition of hydrocinnamic acid was infused for 4 days at doses of 300 to 500 mg/kg of body weight per day. Fetal reticulocytes increased from 10% to 17%. This experiment was repeated with intravenous infusions each day at a dose of 1,000 mg/kg/day for 4 days. Total hemoglobin rose from 6.6 to 7.3 grams/dl, red blood cell count rose from 2.3 to $2.73 \times 10^6$ cells/$\mu$l, and packed red blood cell volume rose from 20.9% to 22.7% of the blood.

Figure 7:
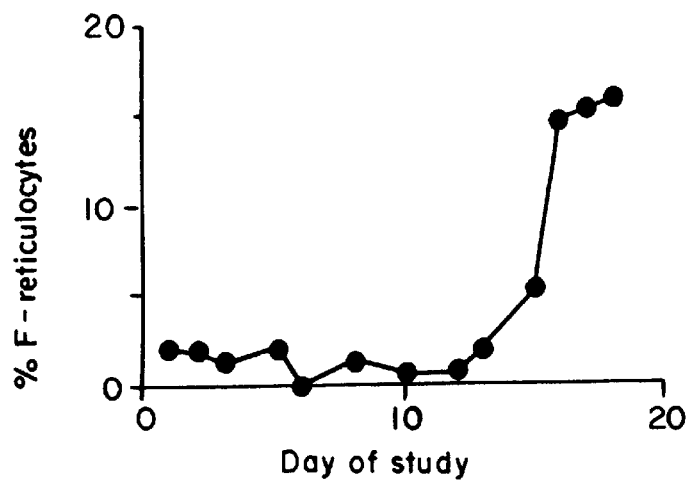
FIG. 7 Daily percent fetal reticulocytes in an anemic baboon treated with phenoxy acetic acid.

A pharmaceutical composition of phenoxyacetic acid was infused each day for 5 days at a dose of 1,500 mg/kg into a baboon (FIG. 7). Total hemoglobin rose from 6.8 to 7.6 grams/dl, packed red blood cell volume rose from 22% to 25.4%, reticulocytes (newly produced red blood cells) increased from 1.9% to 9.2% of all red blood cells and white blood cell count increased from 6.9 to $9.5 \times 10^3$ cells/$\mu$l. The effect maintained itself for two days after drug was discontinued and slowly declined thereafter. This monkey had not responded to arginine butyrate treatments at 1,000 mg/kg for 5 days or 2,000 mg/kg for 3 days.

The experiment was repeated with intravenous infusions at 1,000 to 1,500 mg/kg/day for 4 days into another juvenile baboon. Fetal reticulocytes increased from 2% to 16% or eight-fold (800%) above baseline. Fetal globin protein synthesis increased from 0% to 5% in this short period of time. There was a 4,000% increase in output of fetal globin production over basal levels.

Figure 8:
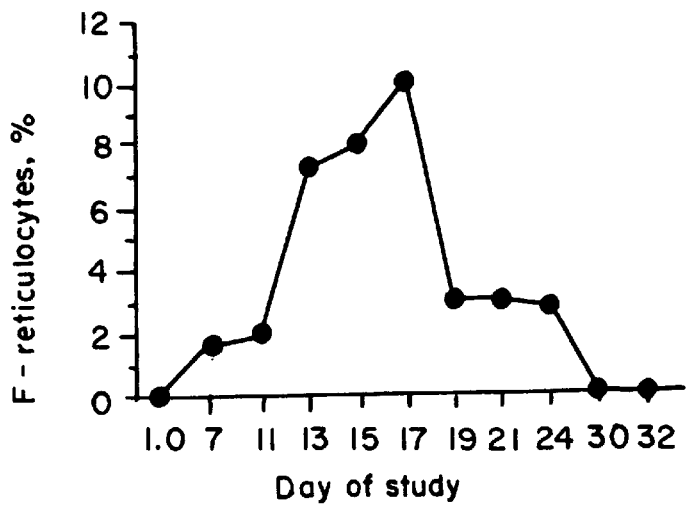
FIG. 8 Daily percent fetal reticulocytes in an anemic baboon treated with α-methyl hydrocinnamic acid.

Another experiment using $\alpha$-methyl hydrocinnamic acid at the same dose was performed on a third baboon. After 5 days, production of fetal hemoglobin producing reticulocytes increased from 0% to 10% (FIG. 8). Fetal globin protein synthesis also increased from 0% to 6.2% of non-alpha globin. No adverse affects were observed.

Figure 9:
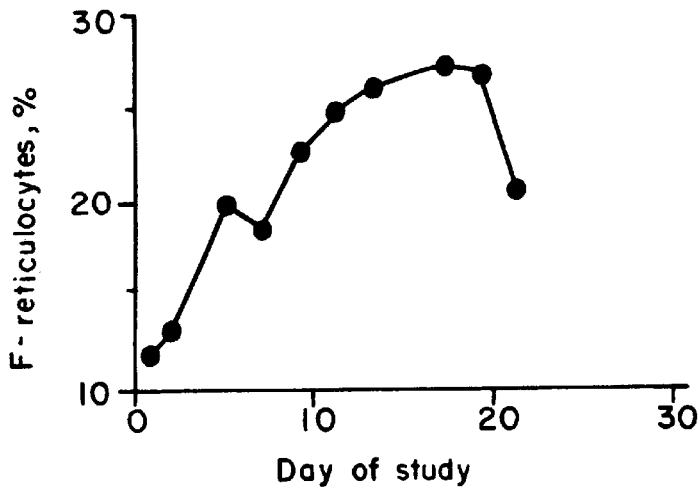
FIG. 9 Daily percent fetal reticulocytes in an anemic baboon treated with phenoxy acetic acid.

A pharmaceutical composition of phenoxyacetic acid was infused into a baboon each day for 5 days at a dose of 500 mg/kg (for 8 hours), 1,000 mg/kg (for 8 hours), and 1,500 mg/kg (for 8 hours). After 3 days, the proportion of fetal reticulocytes, those cells producing fetal hemoglobin, increased from 12% to 27% on treatment (FIG. 9).

Figure 10:
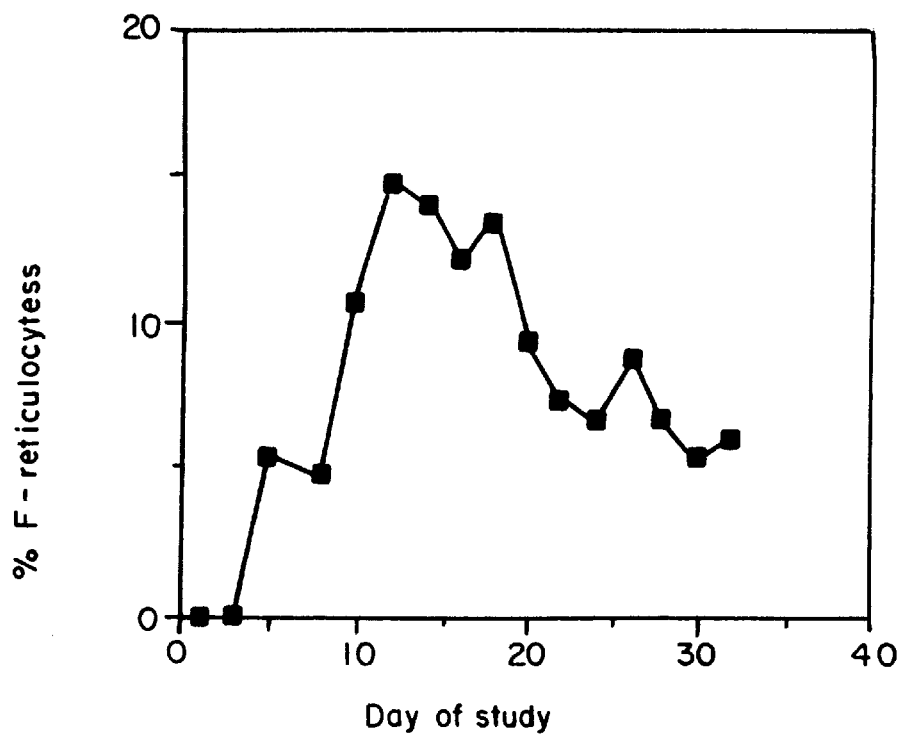
FIG. 10 Daily percent fetal reticulocytes in an anemic baboon treated with steel factor and arginine butyrate.

A pharmaceutical composition of steel (stem cell) factor (R&D Systems; Minneapolis, Minn.) was administered once daily subcutaneously for 4 days at doses of 25 $\mu$g/kg of body weight followed by a wash-out period of three days without any treatment. A second dose of 100 $\mu$g/kg of body weight was given subcutaneously for four days (FIG. 10). Fetal reticulocytes increased from 4% (baseline) to 15% on the first dose regimen and to 12% on the second dose regimen. There was a 3- to 5-fold increase or a 300–500% rise in numbers of newly-formed blood cells producing fetal globin. Fetal globin chain protein also rose 3-fold from being undetectable before treatment to about 3% of total non-alpha globin within the time-frame of the treatment. Consequently, there was a total increase of 9-fold of gamma globin expression in the bone marrow.

Figure 11:
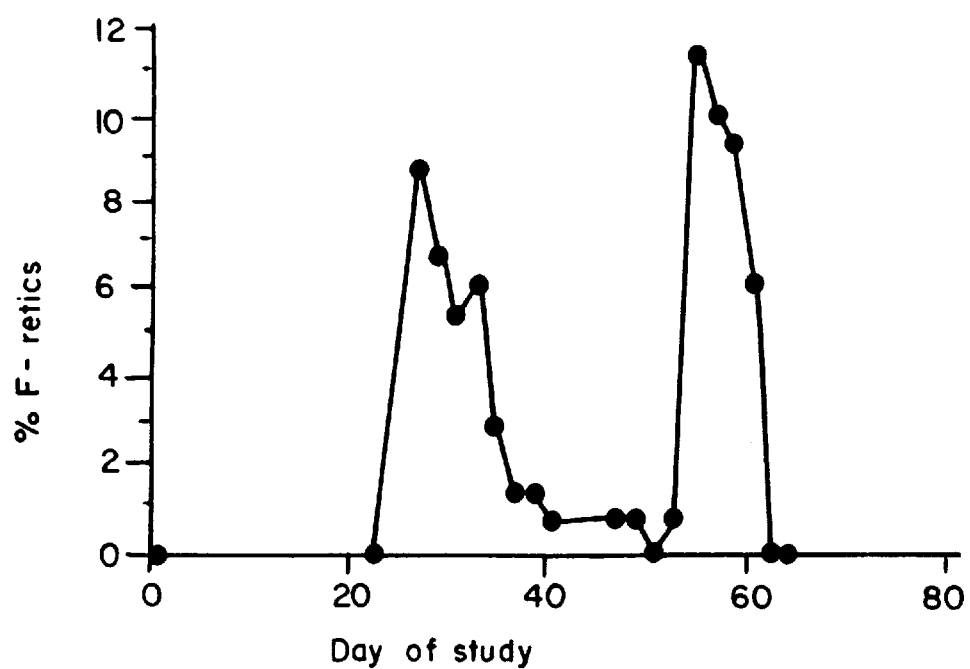
FIG. 11 Daily percent fetal reticulocytes in an anemic baboon treated with butyric acid ethyl ester.

A pharmaceutical composition of butyric acid ethyl ester was infused intravenously for 3 days at doses of 500 to 1,000 mg/kg body weight per day (FIG. 11). Fetal reticulocytes increased by 11.3-fold or over 1,100% above basal levels.

A pharmaceutical composition of monobutyrin (Eastman Kodak; Rochester, N.Y.) was infused intravenously each day for 4 days at doses from 500 to 2,000 mg/kg of body weight. Fetal reticulocytes increased from 12% to 27% or 220% above basal levels. Monobutyrin and isobutyramide were also administered simultaneously at 2,000 and 500 mg/kg day, respectively, for 4 days and demonstrated some synergy.

A pharmaceutical composition of tributyrin was infused intravenously for 3 days at doses of 500 to 750 mg/kg of body weight per day. Fetal reticulocytes increased from 10% to 14%. Gamma globin expression increased from 0% to about 2.2% of total non-alpha globin expression.

A pharmaceutical composition of 3-phenyl butyrate was infused intravenously for 4 days into juvenile baboons at doses of 500 to 1,000 mg/kg of body weight per day.

For comparative purposes, it typically requires about two weeks for hemoglobin to rise 0.5 grams/dl and for packed red blood cell volume to rise by 1.5 to 2% in iron deficiency anemias in humans treated with iron supplements, without any ongoing blood loss. Results found in these phlebotomized monkeys with ongoing blood loss are therefore unusually dramatic and rapid demonstrating that the compositions rapidly stimulate production of all blood cell lineages in an animal model which is extremely close to human. The phenylalkyl acids, which are resistant to metabolic oxidation and filtration by the kidney and are orally bioavailable, should therefore be useful for the treatment of disorders caused by low blood counts, suppression of bone marrow production or increased destruction of blood cells of all lineages.

Example 11
Effects of Compounds on System A Transport

Figure 12A:
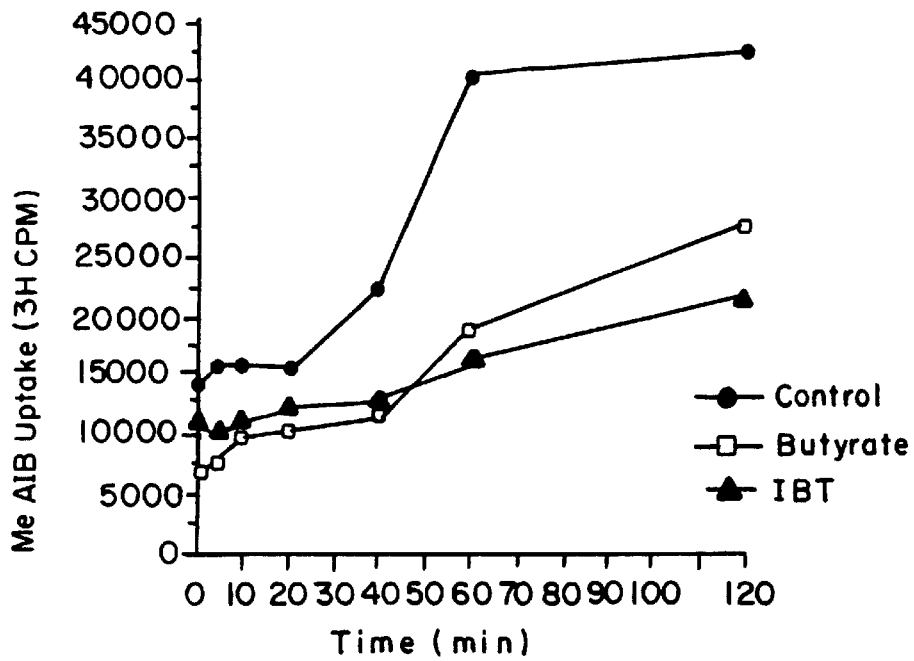
FIG. 12 System A amino acid transport in K562 cells treated with (A) arginine butyrate or isobutyramide, (B) phenoxyacetic acid, or (C) α-methyl hydrocinnamic acid.
Figure 12B:
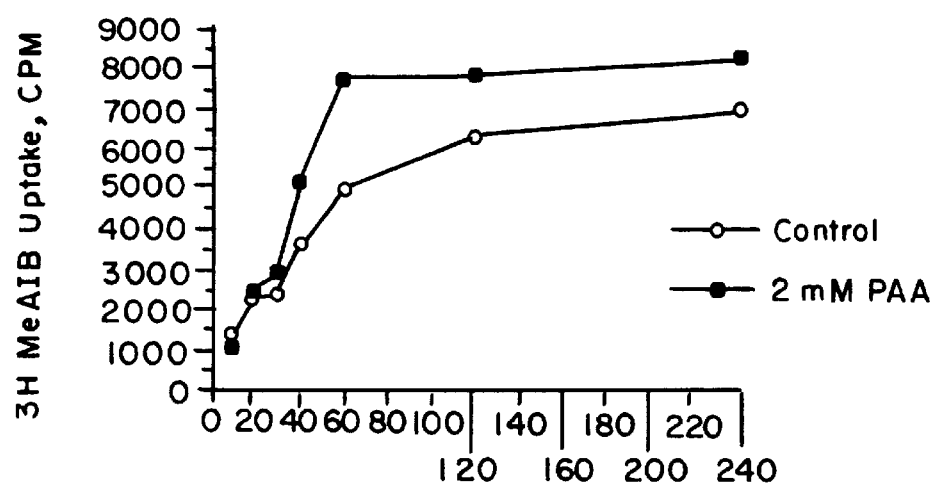
Figure 12C:
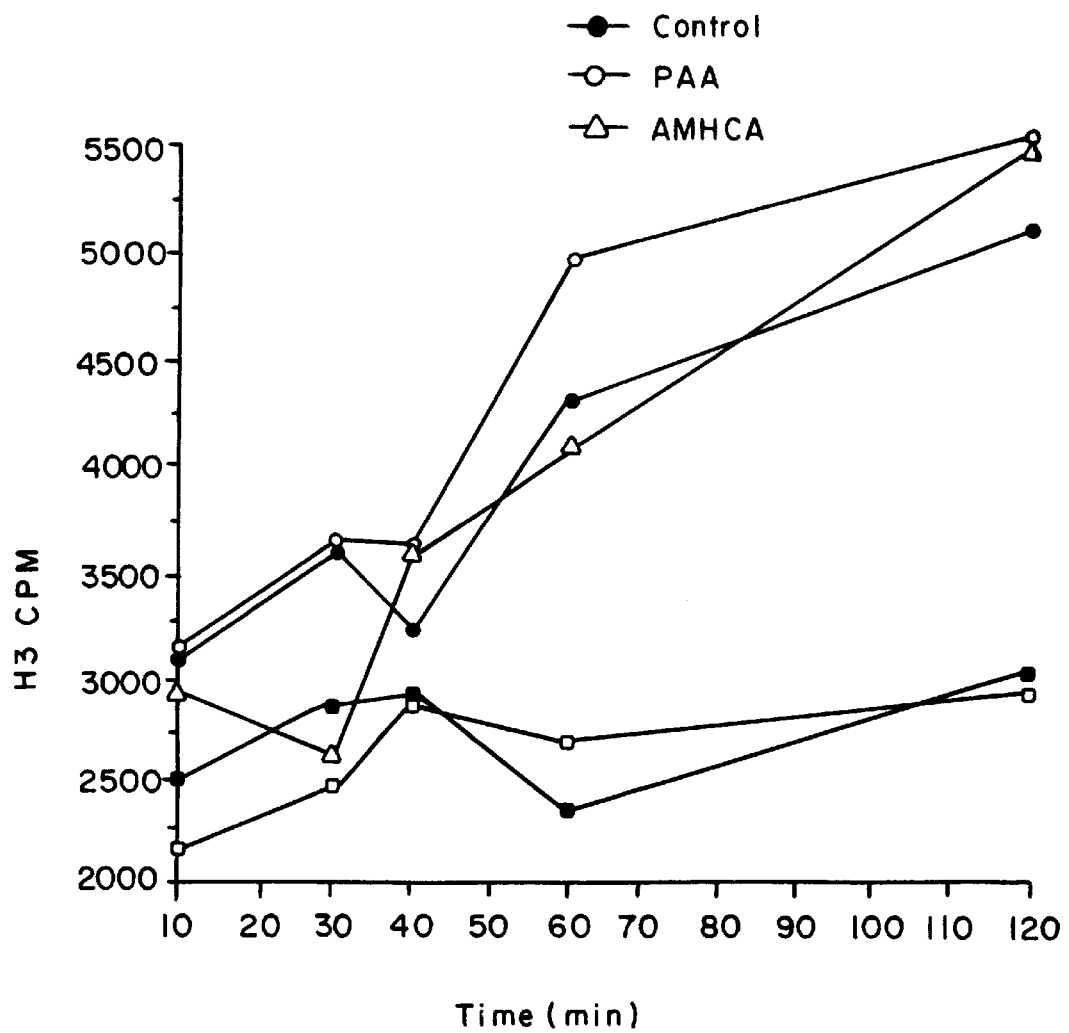

Compositions were tested for their effects on the rate of system A transport (neutral amino acid) in K562 cells and nucleated erythroblasts obtained from fetal liver, previously shown to be comparable in transport to normal erythroid progenitor cells. Inhibition of nutrient uptake is undesirable for treatment of anemias. Methyl aminoisobutyric acid (MAIB) labeled with tritium ($^3$H) is normally taken up by system A amino acid transport. Cold (unlabeled) compounds were added to cultures containing $^3$H-MAIB and incubated for 1 hour. Cells were harvested and the amount of $^3$H taken up by cells was quantitated by scintillation counting. As shown in FIG. 12, isobutyramide and arginine butyrate inhibited the neutral amino acid transport mechanism (FIG. 12A) whereas phenoxy acetic acid and $\alpha$-methyl hydrocinnamic acid and caused no significant inhibition and actually increased uptake of nutrients into cells (FIGS. 12B and 12C). Thus, certain compounds including phenoxyacetic acid and α-methyl hydrocinnamic acid, do not limit uptake of essential amino acids and actually increase uptake of nutrients into cells which would be beneficial for the treatment of all types of anemias regardless of cause.

Example 12
In Vivo Footprinting of the γ-Globin Promoter Region

Levels of γ-globin mRNA increase in response to butyrate treatment in patients with globin disorders (S. P. Perrine et al., N. Engl. J. Med. 328:81–86, 1993). To determine whether this increase was due to the transcriptional modulation of the γ-globin genes and, if so, to examine whether protein-DNA interactions of regulatory sequences for γ-globin gene expression have been changed, in vivo footprinting analysis of the γ-globin gene promoter and HSS-II region of the locus control region (LCR) were performed. The HSS-II region is located upstream of the e-globin gene and has been shown to possess an erythroid-specific powerful enhancer activity in various experimental systems (J. D. Ellis et al., EMBO J. 12:127–34, 1993). Compared to conventional in vitro footprinting methods, which are ordinarily employed to analyze protein-DNA interactions for promoter regions and fail to disclose tissue-specific binding of nuclear proteins to cis-acting elements, in vivo footprinting technique is able to provide bona fide information on transcription factors binding to cis-acting elements that reflects in vivo situations.

Erythroid cell-rich fractions were prepared from patients' peripheral blood or bone marrow before and during treatment, and were in vivo methylated using DMS. Ligation-mediated polymerase chain reaction (LM-PCR) was performed (J. L. Mueller et al., Sci. 246:780–86, 1989). Briefly, 3–7 μg of DNA was suspended in 15 μl of solution A (40 mM Tris-HCl, pH 7.7, 50 mM NaCl) containing 0.6 μmol of primer. First-strand synthesis was performed by adding 7.5 μl of solution B (20 mM $MgCl_2$, 20 mM DTT, 60 μM dNTP) and 1.5 μl of 1:4 diluted Sequenase version 2.0 (United States Biochemical; Cleveland, Ohio) with TE and incubating at 50° C. for 10 minutes. The reaction was quenched by heating at 68° C. for 10 minutes, adding 6 μl of 310 mM Tris-HCl, pH 7.7, and subsequently extracting with phenol/chloroform/isoamyl alcohol (25:24:1) and with ether. Ligation of PCR common linker was performed (P. Moi et al., Proc. Natl. Acad. Sci. USA 87:9000–4, 1990). DNA sequences were amplified by performing 16 to 18 cycles of PCR using 10 μmol each of primer and the longer oligomer of the common linker in a reaction buffer. The amplified products were digested with mung bean nuclease. Footprint ladders were visualized by performing a primer extension using 5' end-labeled primer and subsequently analyzing on 8% urea-polyacrylamide gels. Autoradiograms were established by exposing gels to Kodak XAR films with an intensifying screen. All of the footprints were confirmed by scanning gels with Phosphorimager. All of the footprints were analyzed two or more times to ensure reproducibility.

Figure 13:
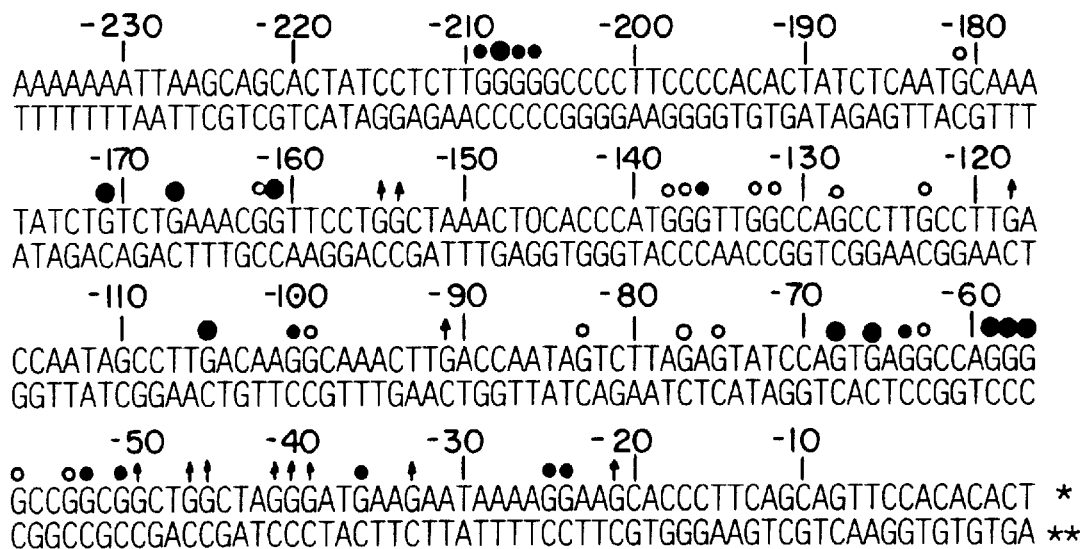
FIG. 13 DNA sequence of the gamma globin gene promoter region with newly protected G residues identified by in vivo footprinting analysis after arginine butyrate treatment marked.

In the γ-globin gene promoter, a DNA fragment extending up to –200 bp relative to the transcription start site is sufficient to direct efficient transcription of the γ-globin genes (K. T. McDonagh et al., J. Biol. Chem. 266:11965–74, 1991; M. J. Urich Blood 75:990–99, 1990). In vivo footprinting analysis for the γ-globin promoter was therefore focused on a region of –200 bp relative to the mRNA cap site. Erythroblasts from a patient with sickle cell anemia, before and after butyrate treatment were analyzed. In the γ-globin promoter, there were no prominent footprints in erythroblasts isolated before treatment, but four major footprints in the fetal response elements (FREs; FRE-γ1 to FRE-γ4), spanning bases –50 to –70, –100 to –110, –155 to –175 and –200 to –210, showing protection of G residues as well as hyper-reactivity over adjacent G residues, were detected from the post-treatment erythroblasts, indicating that arginine butyrate induces multiple transcription factors which interact with the γ-globin gene promoter, resulting in activation (FIG. 13; large black dots (●) represent full protection, smaller black dots (·) represent partial protection, open circles (○) represent unprotected sites, and arrows (↑) represent hyper-reactive G residues). The 3' half of the FRE-γ1 DNA sequence overlaps with the stage-selector element, recently defined in the γ-globin gene promoter, however, the genetic elements defined by FRE-γ2, 3 and 4, have not yet been identified, and may represent the critical elements involved with regulation of these genes.

Figure 14:
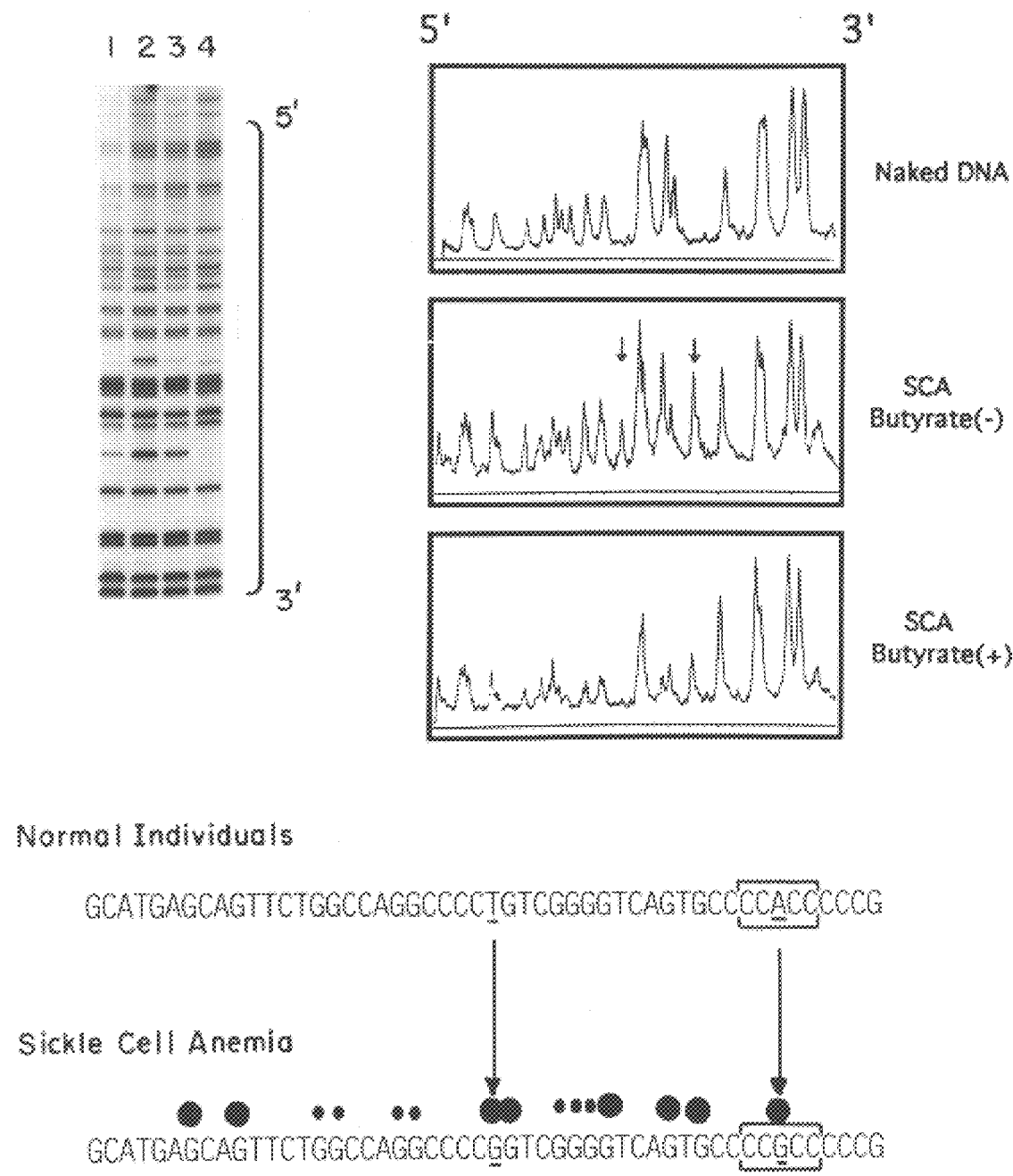
FIG. 14 In vivo footprints over the γ-globin promoter in erythroblasts from untreated and arginine butyrate treated patients with β-thalassemia or sickle cell anemia.

In another experiment, footprints over the γ-globin promoter of erythroblasts from one untreated patient were compared with those of treated patients with β-thalassemia and sickle cell anemia. Footprint ladders of control DNA (lane 1=fetal liver; lane 4=naked DNA) pretreatment (lane 2=SCA without butyrate) and post-treatment (lane 3=SCA with butyrate) are shown in FIG. 14. Following arginine butyrate therapy, the degree of protection on G residues in FRE-γ1 consistently increased.

Figure 15:
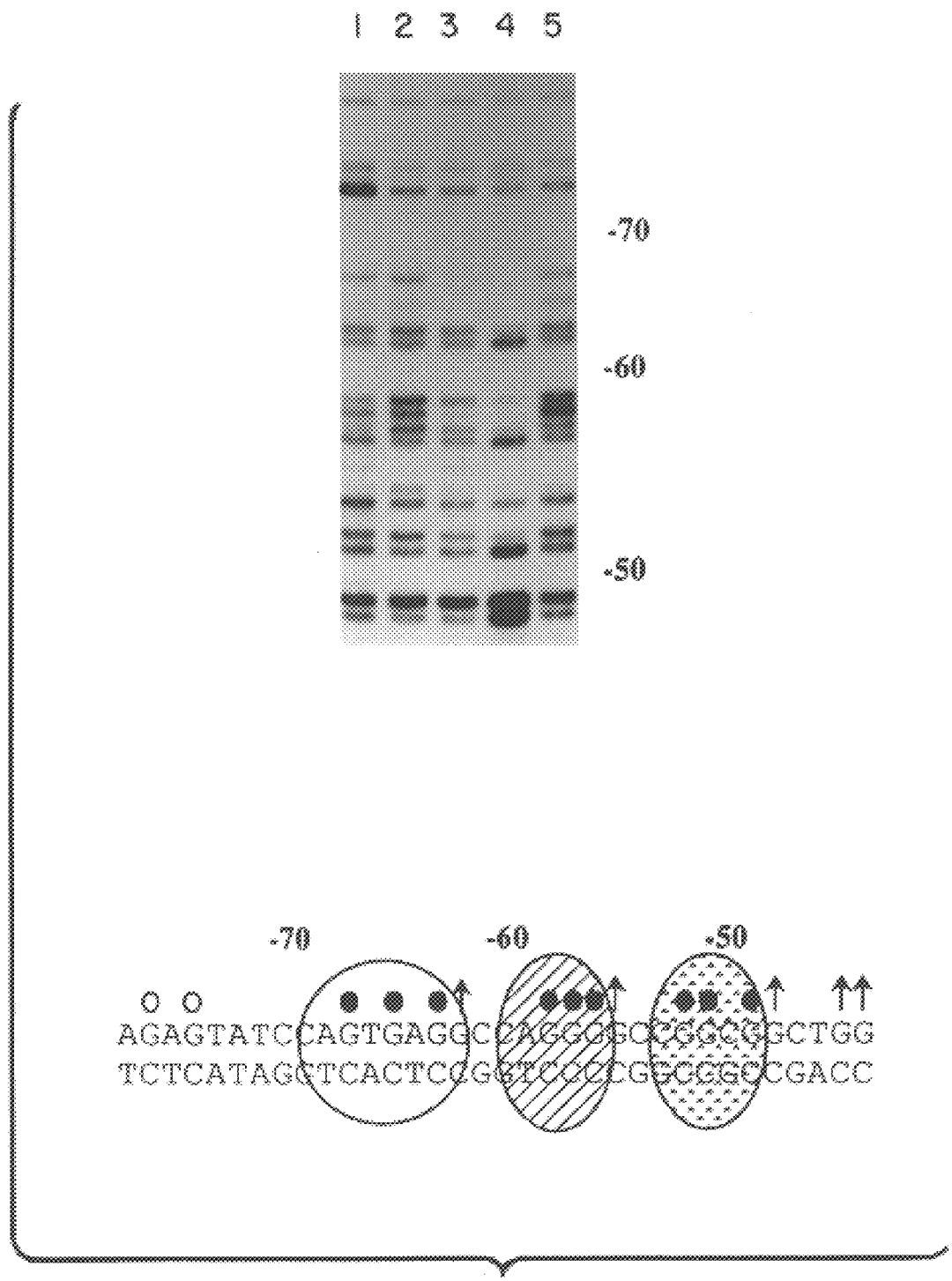
FIG. 15 In vivo footprints over the HSS-II region of the γ-globin promoter region in erythroblasts from untreated or arginine butyrate treated patients with β-thalassemia or sickle cell anemia.

Several lines of evidence obtained from DNA transfection and transgenic experiments have corroborated the functional importance of HSS-II of the LCR in regulating β-like globin gene expression. In vivo footprinting analysis of M62 cells expressing the γ-globin gene revealed extensive protein binding in the γ-globin promoter as well as in HSS-II. In view of these observations, the patterns of in vivo footprints of HSS-II in erythroid cell preparations that were obtained from pre-treatment and post-treatment blood samples were analyzed. Footprint ladders and a summary of the results obtained are shown in FIG. 15 (lane 1=K562 cells; lane 2=before butyrate therapy; lane 3=β-thalassemic after butyrate therapy; lane 4=SCA after butyrate therapy; lane 5=naked DNA). When erythroblasts from a sickle cell patient treated with arginine butyrate were examined, novel in vivo footprints that were not seen in a pre-treatment sample became apparent. New protection was observed over a region spanning about 40 bp, located immediately upstream of the GATA-1 binding sequence (compare lanes 2 and 3 of FIG. 15). The authenticity of these footprints was substantiated by scanning the gel using a Phospholmager. Although the GATA-1 binding sequence has been shown to be footprinted in the embryonic/fetal cell line K562 as well as two human-murine hybrids which express the human γ- or β-globin genes, this motif appears to bind new transcription factors in humans in response to arginine butyrate therapy. This DNA sequence, including the GATA-1 motif, has been designated FRE-HSS-II. FRE-HSS-II, spanning over 40 nucleotides, may comprise multiple individual cis-acting elements, which may work independently or synergistically in regulating the enhancer activity of the HSS-II element. Two nucleotide mutations in this region (shown by arrows in FIG. 15), may influences the binding of transcription factors that modulate enhancer activity of HSS-II. The NF-E2/AP-1 motif, a core cis-acting element for the enhancer activity of HSS-II, was footprinted in all of the cell preparations, regardless of its origin and arginine butyrate treatment. From this data it is apparent that the normal pattern of protein binding to the regulatory sequences of the γ-globin promoter is altered following therapy. This alteration may be responsible for the increased expression of fetal globin mRNA and protein in these patients.

Example 13
Detection of DNA-Binding Regulatory Proteins

The experiments in Example 12 demonstrate that a distinct set of cis-acting elements that reside at the HSS-II and γ-globin promoter are protected by nuclear proteins after arginine butyrate treatment in patients with β-globin disorders. To gain further information on transcription factors binding to FRE elements, gel mobility shift assays with were carried out with promoter fragments containing FRE-γ1. The 3' half of the DNA sequence of FRE-γ1 is overlapped with that of the stage-selector element (SSE) which has recently been identified in the -globin promoter and may be competitively silencing γ-globin gene expression in the fetal stage. Nuclear extracts were purified from a human erythroleukemia cell line, K562, and from erythroblasts that were isolated from peripheral blood or bone marrow of patients. Nuclear extracts used for gel mobility shift assays were prepared as described (Andrews et al., Nucl. Acids Res. 19:2499–2500, 1991). Oligonucleotides, corresponding to the nucleotide sequence from −39 to −78 of the γ-globin promoter (FIG. 13), were annealed to form double-stranded DNA and 5'-labeled with T4 polynucleotide kinase. Prior to addition of a labeled probe, 5 μg of nuclear extracts were mixed with 500 ng of poly(dA-dT) in 20 μl of a binding buffer (25 mM Hepes, pH 7.5, 50 mM KCl 12.5 mM $MgCl_2$, 1 mM DTT, 10 mM $ZnSO_4$, 5% (v/v) glycerol, 1% (v/v) NP-40) at room temperature for 30 minutes. After addition of a labeled probe of $5 \times 10^6$ cpm, the mixture was incubated for 30 minutes at room temperature. Protein-DNA complexes were separated on 5% non-denaturing polyacrylarnide gels in 0.5× TBE at 200V for 90 minutes at room temperature. Gels were dried and exposed to Kodak XAR film overnight without screens.

Figure 16:
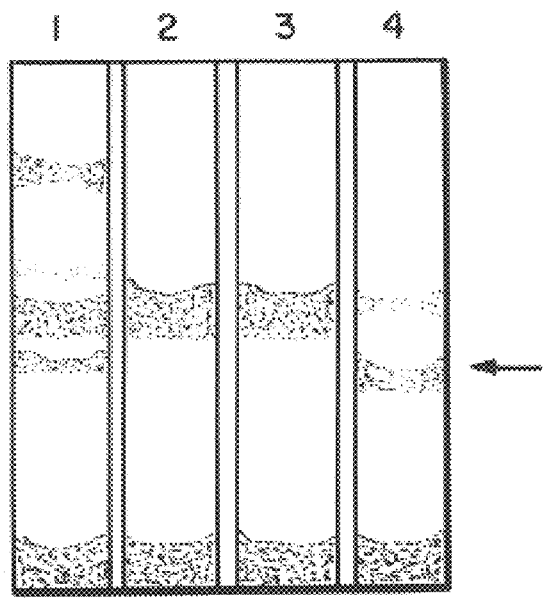
FIG. 16 Gel shift analysis of the proximal region of the γ-globin promoter using nuclear extracts from patients before and during treatment with arginine butyrate and from a normal subject.
Figure 17:
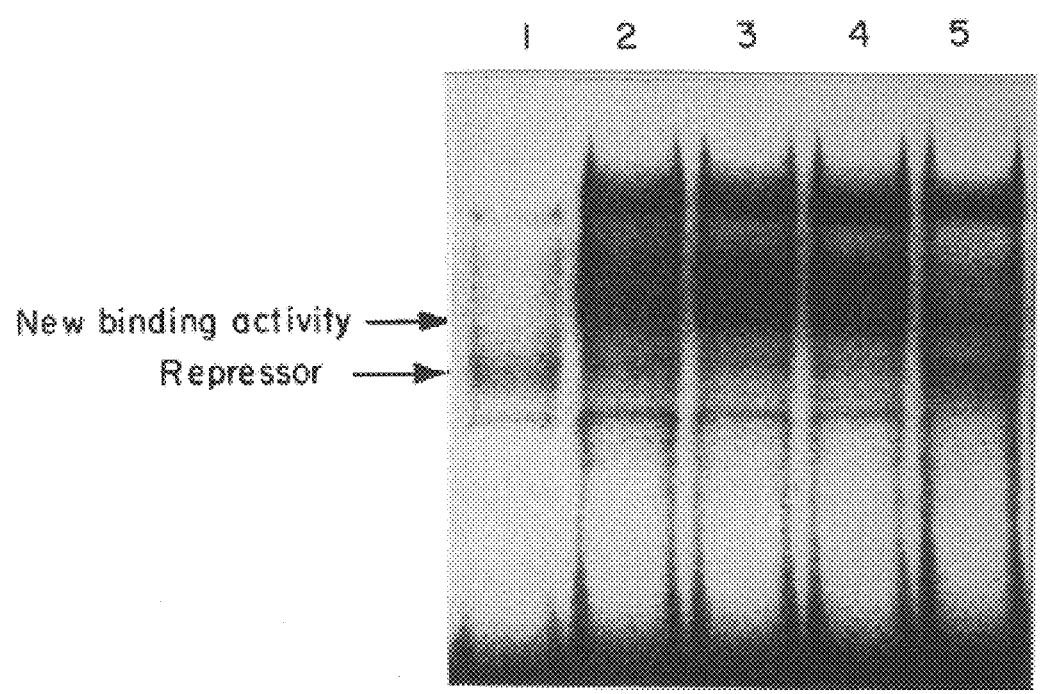
FIG. 17 Gel shift analysis of the proximal region of the γ-globin promoter using nuclear extracts from patients before, during and after treatment with arginine butyrate.

As shown in FIG. 16, lane 1, and FIG. 17, lane 5, nuclear extracts from untreated K562 cells formed three major and two minor protein-DNA complexes. When this DNA probe was incubated with the nuclear extracts from erythroblasts of thalassemic patients, three major protein-DNA complexes were reproducibly formed (FIG. 17, lane 1). Upon butyrate treatment, a new binding activity appeared (FIG. 17, lane 2 {on therapy}, lane 3 {21 hours after therapy}, and lane 4 {43 hours after therapy}), while another binding activity, present in the untreated patients' samples (FIG. 17, lane 1), and in a normal subject's marrow (FIG. 16, lane 4), disappeared. The new binding activity likely represents a transcriptional activator induced by treatment with the compounds, whereas disappearance of the other binding activity, present in the erythroblasts of patients with low or no γ-globin gene expression may represent the loss of a transcriptional repressor in response to treatment. Nuclear extracts from a patient with sickle cell anemia who did not respond to butyrate treatment exhibited no increase in the intensity of the activator band or loss of the repressor band.

Example 14
The FRE-γ1 Element Confers Inducibility to Treatment

Functional assay underscores the important role of FRE-γ1 in γ-globin gene expression in K562 cells. To ascertain whether the FRE elements of the γ-globin promoter that were identified by in vivo footprinting were indeed involved in arginine butyrate inducibility for γ-globin gene expression, a series of 5' deletion constructs of the γ-globin promoter, extending from −256 to −61, were constructed and linked them to the NEO gene. Activity of the NEO gene of these constructs, in response to arginine butyrate treatment, was examined by transfecting these reporters into K562 cells. In K562 cells, a construct driven by 256 bp of promoter was able to direct NEO activity expression, resulting in colony formation. Deletion to −199 of the promoter from the cap site, which removed FRE-γ4, did not alter expression of the NEO gene. Deletion to position −61 reduced promoter activity to 33–40% of the activity seen with the −256 bp construct. Treatment with arginine butyrate or isobutyramide induced the activity of this construct by 2.5 to 4 fold, suggesting that this proximal region of the γ-globin promoter, containing the FRE-γ1 element, is able to endow the γ-globin gene with inducibility by these compounds.

Example 15
Molecular Characterization of Transcription Factors

Transcription factors are purified from human erythroblasts or erythroid cell line extracts prepared as described by N. C. Andrews et al. (Nature 362:722, 1993). Briefly, extracts are tested for binding activity to an oligonucleotide containing the binding site sequence, and positive fractions subjected to sodium dodecylsulfate polyacrylamide gel electrophoresis (SDS-PAGE). Two different approaches are utilized to clone the genes which encode the transcription factors. First, a human fetal liver lamda gt11 expression library is screened with $^{32}P$-radiolabeled oligonucleotides containing the binding sequence. Positive plaques are purified and recombinant inserts isolated and sequenced. Alternatively, transcription factor genes are cloned by creating antibodies to the purified protein. A human fetal liver lamda gt 11 expression library is screened with a labeled antibody specific to the protein and positive clones identified, cloned and sequenced.

Other embodiments and uses of the invention will be apparent to those skilled in the art from consideration of the specification and practice of the invention disclosed herein. The specification and examples should be considered exemplary only with the true scope and spirit of the invention indicated by the following claims.

We claim:

1. A pharmaceutical composition comprising (1) a chemical compound, wherein the chemical compound is thiophenoxy acetic acid, thiophenoxy propionic acid or thiophenoxy butyric acid, (2) a hematopoietic protein on a positive hemoglobin modulating agent and (3) a pharmaceutically acceptable carrier.

2. The composition of claim 1 wherein the pharmaceutically acceptable carrier is selected from the group consisting of water, alcohols, oils, salts, fatty acids, saccharides, polysaccharides and combinations thereof.

3. A pharmaceutical combination comprising:
   (1) butyric acid ethyl ester and pharmaceutically acceptable salts thereof;
   (2) a hematopoietic protein or a positive hemoglobin modulating agent; and
   (3) a pharmaceutically acceptable carrier or diluent.

4. A pharmaceutical combination comprising:
   (1) dihydrocinnamic acid and pharmaceutically acceptable salts thereof;
   (2) a hematopoietic protein or a positive hemoglobin modulating agent; and
   (3) a pharmaceutically acceptable carrier or diluent.

5. A pharmaceutical combination comprising:
   (1) dihydrocinnamic acid and pharmaceutically acceptable salts thereof;
   (2) erythropoietin; and
   (3) a pharmaceutically acceptable carrier or diluent.

6. A pharmaceutical combination comprising (1) butyric acid ethyl ester, and pharmaceutically acceptable salts thereof: (2) erythropoietin; and (3) a pharmaceutically acceptable carrier or diluent.

7. A pharmaceutical combination comprising:
(1) thiophenoxyacetic acid and pharmaceutically acceptable salts thereof;
(2) a hematopoietic protein or positive hemoglobin modulating agent; and
(3) a pharmaceutically acceptable carrier or diluent.

8. A pharmaceutical combination comprising:
(1) thiophenoxyacetic acid and pharmaceutically acceptable salts thereof;
(2) erythropoietin; and
(3) a pharmaceutically acceptable carrier or diluent.

9. A pharmaceutical combination comprising:
(1) α-methyl hydrocinnamic acid and pharmaceutically acceptable salts thereof;
(2) a hematopoietic protein or positive hemoglobin modulating agent; and
(3) a pharmaceutically acceptable carrier or diluent.

10. A pharmaceutical combination comprising:
(1) α-methyl hydrocinnamic acid and pharmaceutically acceptable salts thereof:
(2) erythropoietin; and
(3) a pharmaceutically acceptable carrier or diluent.

* * * * *